United States Patent
Martin et al.

(10) Patent No.: US 9,931,128 B2
(45) Date of Patent: Apr. 3, 2018

(54) METHODS FOR RESTORING BLOOD FLOW WITHIN BLOCKED VASCULATURE

(71) Applicant: Covidien LP, Mansfield, MA (US)

(72) Inventors: Brian B. Martin, Felton, CA (US); Martin S. Dieck, Campbell, CA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 14/038,461

(22) Filed: Sep. 26, 2013

(65) Prior Publication Data
US 2014/0188143 A1 Jul. 3, 2014

Related U.S. Application Data

(63) Continuation of application No. 11/684,546, filed on Mar. 9, 2007, now abandoned, which is a continuation of application No. 11/671,450, filed on Feb. 5, 2007, now abandoned.

(60) Provisional application No. 60/765,496, filed on Feb. 3, 2006.

(51) Int. Cl.
*A61B 17/221* (2006.01)
*A61B 17/22* (2006.01)
*A61B 17/00* (2006.01)

(52) U.S. Cl.
CPC ...... *A61B 17/221* (2013.01); *A61B 17/22012* (2013.01); *A61B 2017/00862* (2013.01); *A61B 2017/00867* (2013.01); *A61B 2017/2212* (2013.01); *A61B 2017/2215* (2013.01); *A61B 2017/22034* (2013.01); *A61B 2017/22051* (2013.01); *A61B 2017/22094* (2013.01)

(58) Field of Classification Search
CPC ...... A61B 17/32075; A61B 17/320725; A61B 17/32056; A61B 17/221; A61B 2017/22034; A61B 2017/22035; A61B 2017/22031; A61B 2017/22094; A61F 2/013
See application file for complete search history.

(56) References Cited

U.S. PATENT DOCUMENTS

| | | |
|---|---|---|
| 2,918,919 A | 12/1959 | Wallace |
| 2,943,626 A | 7/1960 | Dormia |
| 3,996,938 A | 12/1976 | Clark |
| 4,347,846 A | 9/1982 | Dormia |
| 4,611,594 A | 9/1986 | Grayhack et al. |
| 4,650,466 A | 3/1987 | Luther |
| 4,699,147 A | 10/1987 | Chilson et al. |
| 4,790,812 A | 12/1988 | Hawkins, Jr. et al. |
| 4,807,626 A | 2/1989 | McGirr |
| 4,832,055 A | 5/1989 | Palestrant |
| 4,873,978 A | 10/1989 | Ginsburg |
| 4,969,891 A | 11/1990 | Gewertz |

(Continued)

FOREIGN PATENT DOCUMENTS

| | | |
|---|---|---|
| CN | 102036611 A | 4/2011 |
| DE | 3501707 | 7/1986 |

(Continued)

*Primary Examiner* — Sarah W Aleman
(74) *Attorney, Agent, or Firm* — Fortem IP LLP; Mary Fox

(57) ABSTRACT

The devices and methods described herein relate to clearing of blockages within body lumens, such as the vasculature, by addressing the frictional resistance on the obstruction prior to attempting to translate and/or mobilize the obstruction within the body lumen.

22 Claims, 19 Drawing Sheets

(56) References Cited

U.S. PATENT DOCUMENTS

| | | |
|---|---|---|
| 4,998,539 A | 3/1991 | Delsanti |
| 5,034,001 A | 7/1991 | Garrison et al. |
| 5,057,114 A | 10/1991 | Wittich et al. |
| 5,059,178 A | 10/1991 | Ya |
| 5,102,415 A | 4/1992 | Guenther et al. |
| 5,147,400 A | 9/1992 | Kaplan et al. |
| 5,152,777 A | 10/1992 | Goldberg et al. |
| 5,192,286 A * | 3/1993 | Phan et al. ............ 606/127 |
| 5,300,086 A | 4/1994 | Gory et al. |
| 5,329,942 A | 7/1994 | Gunther et al. |
| 5,443,478 A | 8/1995 | Purdy |
| 5,449,372 A | 9/1995 | Schmaltz et al. |
| 5,458,375 A | 10/1995 | Anspach et al. |
| 5,490,859 A | 2/1996 | Mische et al. |
| 5,496,330 A | 3/1996 | Bates et al. |
| 5,509,900 A | 4/1996 | Kirkman |
| 5,653,684 A | 8/1997 | Laptewicz et al. |
| 5,658,296 A | 8/1997 | Bates et al. |
| 5,709,704 A | 1/1998 | Nott et al. |
| 5,733,302 A | 3/1998 | Myler et al. |
| 5,741,325 A | 4/1998 | Chaikof et al. |
| 5,792,156 A | 8/1998 | Perouse |
| 5,827,324 A | 10/1998 | Cassell et al. |
| 5,846,251 A | 12/1998 | Hart |
| 5,895,398 A | 4/1999 | Wensel et al. |
| 5,941,869 A | 8/1999 | Patterson et al. |
| 5,947,995 A | 9/1999 | Samuels |
| 5,968,090 A | 10/1999 | Ratcliff et al. |
| 5,971,938 A | 10/1999 | Hart et al. |
| 5,972,019 A * | 10/1999 | Engelson et al. ............ 606/200 |
| 5,984,957 A | 11/1999 | Laptewicz et al. |
| 6,001,118 A | 12/1999 | Daniel et al. |
| 6,033,394 A | 3/2000 | Vidlund et al. |
| 6,042,598 A | 3/2000 | Tsugita et al. |
| 6,053,932 A | 4/2000 | Daniel et al. |
| 6,066,149 A | 5/2000 | Samson et al. |
| 6,066,158 A | 5/2000 | Engelson et al. |
| 6,096,053 A | 8/2000 | Bates |
| 6,099,534 A | 8/2000 | Bates et al. |
| 6,146,403 A | 11/2000 | St. Germain |
| 6,159,220 A | 12/2000 | Gobron et al. |
| 6,165,200 A | 12/2000 | Tsugita et al. |
| 6,168,570 B1 | 1/2001 | Ferrera |
| 6,168,603 B1 | 1/2001 | Leslie et al. |
| 6,174,318 B1 | 1/2001 | Bates et al. |
| 6,176,873 B1 | 1/2001 | Ouchi |
| 6,190,394 B1 | 2/2001 | Lind et al. |
| 6,217,609 B1 | 4/2001 | Haverkost |
| 6,221,006 B1 | 4/2001 | Dubrul et al. |
| 6,245,088 B1 | 6/2001 | Lowery |
| 6,245,089 B1 | 6/2001 | Daniel et al. |
| 6,248,113 B1 | 6/2001 | Fina |
| 6,264,664 B1 | 7/2001 | Avellanet |
| 6,302,895 B1 | 10/2001 | Gobron et al. |
| 6,309,399 B1 | 10/2001 | Barbut et al. |
| 6,348,056 B1 | 2/2002 | Bates et al. |
| 6,350,266 B1 | 2/2002 | White et al. |
| 6,364,895 B1 | 4/2002 | Greenhalgh |
| 6,371,971 B1 | 4/2002 | Tsugita et al. |
| 6,383,195 B1 | 5/2002 | Richard |
| 6,383,196 B1 | 5/2002 | Leslie et al. |
| 6,391,044 B1 | 5/2002 | Yadav et al. |
| 6,402,771 B1 | 6/2002 | Palmer et al. |
| 6,409,750 B1 | 6/2002 | Hyodoh et al. |
| 6,416,505 B1 | 7/2002 | Fleischman et al. |
| 6,425,909 B1 | 7/2002 | Dieck et al. |
| 6,436,112 B2 | 8/2002 | Wensel et al. |
| 6,443,972 B1 | 9/2002 | Bosma et al. |
| 6,458,139 B1 | 10/2002 | Palmer et al. |
| 6,475,169 B2 | 11/2002 | Ferrera |
| 6,485,497 B2 | 11/2002 | Wensel et al. |
| 6,494,884 B2 | 12/2002 | Gifford, III et al. |
| 6,506,204 B2 | 1/2003 | Mazzocchi |
| 6,514,273 B1 | 2/2003 | Voss et al. |
| 6,530,935 B2 | 3/2003 | Wensel et al. |
| 6,540,657 B2 | 4/2003 | Cross, III et al. |
| 6,540,768 B1 | 4/2003 | Diaz et al. |
| 6,551,342 B1 | 4/2003 | Shen et al. |
| 6,575,997 B1 | 6/2003 | Palmer et al. |
| 6,585,753 B2 | 7/2003 | Eder et al. |
| 6,592,605 B2 | 7/2003 | Lenker et al. |
| 6,592,607 B1 | 7/2003 | Palmer et al. |
| 6,602,271 B2 | 8/2003 | Adams et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,620,148 B1 | 9/2003 | Tsugita |
| 6,635,068 B1 | 10/2003 | Dubrul et al. |
| 6,636,758 B2 | 10/2003 | Sanchez et al. |
| 6,638,245 B2 | 10/2003 | Miller et al. |
| 6,638,293 B1 | 10/2003 | Makower et al. |
| 6,641,590 B1 | 11/2003 | Palmer et al. |
| 6,645,199 B1 | 11/2003 | Jenkins et al. |
| 6,652,505 B1 | 11/2003 | Tsugita |
| 6,652,548 B2 | 11/2003 | Evans et al. |
| 6,660,021 B1 | 12/2003 | Palmer et al. |
| 6,663,650 B2 | 12/2003 | Sepetka et al. |
| 6,673,042 B1 | 1/2004 | Samson et al. |
| 6,679,893 B1 | 1/2004 | Tran |
| 6,685,738 B2 | 2/2004 | Chouinard et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,730,104 B1 | 5/2004 | Sepetka et al. |
| 6,745,080 B2 | 6/2004 | Koblish |
| 6,746,468 B1 | 6/2004 | Sepetka et al. |
| 6,749,619 B2 | 6/2004 | Ouriel et al. |
| 6,755,813 B2 | 6/2004 | Ouriel et al. |
| 6,800,080 B1 | 10/2004 | Bates |
| 6,824,545 B2 | 11/2004 | Sepetka et al. |
| 6,855,155 B2 | 2/2005 | Denardo et al. |
| 6,872,211 B2 | 3/2005 | White et al. |
| 6,872,216 B2 | 3/2005 | Daniel et al. |
| 6,890,341 B2 | 5/2005 | Dieck et al. |
| 6,893,431 B2 | 5/2005 | Naimark et al. |
| 6,905,503 B2 | 6/2005 | Gifford, III et al. |
| 6,913,612 B2 | 7/2005 | Palmer et al. |
| 6,936,059 B2 | 8/2005 | Belef |
| 6,939,362 B2 | 9/2005 | Boyle et al. |
| 6,945,977 B2 | 9/2005 | Demarais et al. |
| 6,953,465 B2 | 10/2005 | Dieck et al. |
| 6,964,672 B2 | 11/2005 | Brady et al. |
| 7,004,955 B2 | 2/2006 | Shen et al. |
| 7,004,956 B2 | 2/2006 | Palmer et al. |
| 7,037,320 B2 | 5/2006 | Brady et al. |
| 7,041,126 B2 | 5/2006 | Shin et al. |
| 7,048,014 B2 | 5/2006 | Hyodoh et al. |
| 7,058,456 B2 | 6/2006 | Pierce |
| 7,097,653 B2 | 8/2006 | Freudenthal et al. |
| 7,101,380 B2 | 9/2006 | Khachin et al. |
| 7,169,165 B2 | 1/2007 | Belef et al. |
| 7,179,273 B1 | 2/2007 | Palmer et al. |
| 7,182,771 B1 | 2/2007 | Houser et al. |
| 7,235,061 B2 | 6/2007 | Tsugita |
| 7,240,516 B2 | 7/2007 | Pryor |
| 7,279,000 B2 | 10/2007 | Cartier et al. |
| 7,285,126 B2 | 10/2007 | Sepetka et al. |
| 7,286,866 B2 | 10/2007 | Okerlund et al. |
| 7,288,112 B2 | 10/2007 | Denardo et al. |
| 7,294,311 B2 | 11/2007 | Coville |
| 7,300,428 B2 | 11/2007 | Ingenito |
| 7,303,758 B2 | 12/2007 | Falotico et al. |
| 7,306,619 B1 | 12/2007 | Palmer |
| 7,314,477 B1 | 1/2008 | Ravenscroft et al. |
| 7,314,728 B2 | 1/2008 | Toombs |
| 7,316,692 B2 | 1/2008 | Huffmaster |
| 7,329,265 B2 | 2/2008 | Burbank et al. |
| 7,332,330 B2 | 2/2008 | Humes et al. |
| 7,341,569 B2 | 3/2008 | Soltani et al. |
| 7,344,550 B2 | 3/2008 | Carrison et al. |
| 7,367,982 B2 | 5/2008 | Nash et al. |
| 7,399,308 B2 | 7/2008 | Borillo et al. |
| 7,491,210 B2 | 2/2009 | Dubrul et al. |

(56) References Cited

U.S. PATENT DOCUMENTS

| | | |
|---|---|---|
| 7,534,252 B2 | 5/2009 | Sepetka et al. |
| 7,578,830 B2 | 8/2009 | Kusleika et al. |
| 7,621,870 B2 | 11/2009 | Berrada et al. |
| 7,837,702 B2 | 11/2010 | Bates |
| 8,070,791 B2 | 12/2011 | Ferrera et al. |
| 8,088,140 B2 | 1/2012 | Ferrera et al. |
| 8,105,333 B2 | 1/2012 | Sepetka et al. |
| 8,197,493 B2 | 6/2012 | Ferrera et al. |
| 8,545,526 B2 | 10/2013 | Martin et al. |
| 2001/0041909 A1 | 11/2001 | Tsugita et al. |
| 2001/0044632 A1 | 11/2001 | Daniel et al. |
| 2001/0044634 A1 | 11/2001 | Don et al. |
| 2001/0051810 A1 | 12/2001 | Dubrul et al. |
| 2002/0002396 A1 | 1/2002 | Fulkerson |
| 2002/0004667 A1 | 1/2002 | Adams et al. |
| 2002/0026211 A1 | 2/2002 | Khosravi et al. |
| 2002/0058904 A1 | 5/2002 | Boock et al. |
| 2002/0062135 A1 | 5/2002 | Mazzocchi et al. |
| 2002/0072764 A1 | 6/2002 | Sepetka et al. |
| 2002/0082558 A1 | 6/2002 | Samson et al. |
| 2002/0123765 A1 | 9/2002 | Sepetka et al. |
| 2002/0138094 A1 | 9/2002 | Borillo et al. |
| 2002/0143349 A1 | 10/2002 | Gifford et al. |
| 2002/0151928 A1 | 10/2002 | Leslie et al. |
| 2002/0169473 A1 | 11/2002 | Sepetka et al. |
| 2002/0169474 A1 | 11/2002 | Kusleika et al. |
| 2002/0188314 A1 | 12/2002 | Anderson et al. |
| 2002/0193812 A1 | 12/2002 | Patel et al. |
| 2002/0193813 A1 | 12/2002 | Helkowski et al. |
| 2002/0193825 A1 | 12/2002 | McGuckin et al. |
| 2003/0004533 A1 | 1/2003 | Dieck et al. |
| 2003/0004542 A1 | 1/2003 | Wensel et al. |
| 2003/0004568 A1 | 1/2003 | Ken et al. |
| 2003/0023265 A1 | 1/2003 | Forber |
| 2003/0040771 A1 | 2/2003 | Hyodoh et al. |
| 2003/0050663 A1 | 3/2003 | Khachin et al. |
| 2003/0060782 A1 | 3/2003 | Bose et al. |
| 2003/0093087 A1 | 5/2003 | Jones et al. |
| 2003/0093111 A1 | 5/2003 | Ken et al. |
| 2003/0144687 A1 | 7/2003 | Brady et al. |
| 2003/0153935 A1 | 8/2003 | Mialhe |
| 2003/0176884 A1 | 9/2003 | Berrada et al. |
| 2003/0195556 A1 | 10/2003 | Stack et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0098024 A1 | 5/2004 | Dieck et al. |
| 2004/0133232 A1 | 7/2004 | Rosenbluth et al. |
| 2004/0138692 A1 | 7/2004 | Phung et al. |
| 2004/0153025 A1 | 8/2004 | Seifert et al. |
| 2004/0153118 A1 | 8/2004 | Clubb et al. |
| 2004/0161451 A1 | 8/2004 | Pierce et al. |
| 2004/0172056 A1 | 9/2004 | Guterman et al. |
| 2004/0199201 A1 | 10/2004 | Kellett et al. |
| 2004/0199243 A1 | 10/2004 | Yodfat |
| 2004/0210116 A1 | 10/2004 | Nakao |
| 2004/0267301 A1 | 12/2004 | Boylan et al. |
| 2005/0004594 A1 | 1/2005 | Nool et al. |
| 2005/0033348 A1 | 2/2005 | Sepetka et al. |
| 2005/0038447 A1 | 2/2005 | Huffmaster |
| 2005/0043680 A1 | 2/2005 | Segal et al. |
| 2005/0043756 A1 | 2/2005 | Lavelle et al. |
| 2005/0049619 A1* | 3/2005 | Sepetka ............ A61B 17/22031 606/159 |
| 2005/0055033 A1 | 3/2005 | Leslie et al. |
| 2005/0055047 A1 | 3/2005 | Greenhalgh |
| 2005/0059995 A1 | 3/2005 | Sepetka et al. |
| 2005/0080356 A1 | 4/2005 | Dapolito et al. |
| 2005/0085826 A1 | 4/2005 | Nair et al. |
| 2005/0085847 A1 | 4/2005 | Galdonik et al. |
| 2005/0085849 A1 | 4/2005 | Sepetka et al. |
| 2005/0090857 A1 | 4/2005 | Kusleika et al. |
| 2005/0090858 A1 | 4/2005 | Pavlovic |
| 2005/0125024 A1 | 6/2005 | Sepetka et al. |
| 2005/0131450 A1 | 6/2005 | Nicholson et al. |
| 2005/0137680 A1 | 6/2005 | Ortiz et al. |
| 2005/0171566 A1 | 8/2005 | Kanamaru |
| 2005/0203571 A1 | 9/2005 | Mazzocchi et al. |
| 2005/0209609 A1 | 9/2005 | Wallace |
| 2005/0216030 A1 | 9/2005 | Sepetka et al. |
| 2005/0216050 A1* | 9/2005 | Sepetka et al. ............... 606/200 |
| 2005/0222580 A1 | 10/2005 | Gifford, III et al. |
| 2005/0228417 A1 | 10/2005 | Teitelbaum et al. |
| 2005/0234501 A1 | 10/2005 | Barone |
| 2005/0234505 A1 | 10/2005 | Diaz et al. |
| 2005/0277978 A1 | 12/2005 | Greenhalgh |
| 2005/0283166 A1 | 12/2005 | Greenhalgh |
| 2005/0283182 A1 | 12/2005 | Pierce et al. |
| 2005/0283186 A1 | 12/2005 | Berrada et al. |
| 2005/0288686 A1 | 12/2005 | Sepetka et al. |
| 2006/0004404 A1 | 1/2006 | Khachin et al. |
| 2006/0009784 A1 | 1/2006 | Behl et al. |
| 2006/0036280 A1 | 2/2006 | French et al. |
| 2006/0047286 A1 | 3/2006 | West |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0095070 A1 | 5/2006 | Gilson et al. |
| 2006/0129166 A1 | 6/2006 | Lavelle |
| 2006/0129180 A1 | 6/2006 | Tsugita et al. |
| 2006/0155305 A1 | 7/2006 | Freudenthal et al. |
| 2006/0190070 A1 | 8/2006 | Dieck et al. |
| 2006/0195137 A1 | 8/2006 | Sepetka et al. |
| 2006/0229638 A1 | 10/2006 | Abrams et al. |
| 2006/0253145 A1 | 11/2006 | Lucas |
| 2006/0276805 A1 | 12/2006 | Yu |
| 2006/0282111 A1 | 12/2006 | Morsi |
| 2006/0287668 A1 | 12/2006 | Fawzi et al. |
| 2007/0112374 A1 | 5/2007 | Paul et al. |
| 2007/0118165 A1 | 5/2007 | DeMello et al. |
| 2007/0149996 A1 | 6/2007 | Coughlin |
| 2007/0185500 A1 | 8/2007 | Martin et al. |
| 2007/0185501 A1 | 8/2007 | Martin et al. |
| 2007/0197103 A1 | 8/2007 | Martin et al. |
| 2007/0198029 A1 | 8/2007 | Martin et al. |
| 2007/0198030 A1 | 8/2007 | Martin et al. |
| 2007/0198051 A1 | 8/2007 | Clubb et al. |
| 2007/0208367 A1 | 9/2007 | Fiorella et al. |
| 2007/0208371 A1 | 9/2007 | French et al. |
| 2007/0225749 A1 | 9/2007 | Martin et al. |
| 2007/0233236 A1 | 10/2007 | Pryor |
| 2007/0258971 A1 | 11/2007 | Heslet et al. |
| 2007/0265656 A1 | 11/2007 | Amplatz et al. |
| 2007/0270905 A1 | 11/2007 | Osborne |
| 2008/0015541 A1 | 1/2008 | Rosenbluth et al. |
| 2008/0050389 A1 | 2/2008 | Muzykantov et al. |
| 2008/0051708 A1 | 2/2008 | Kumar et al. |
| 2008/0058256 A1 | 3/2008 | Boone et al. |
| 2008/0065012 A1 | 3/2008 | Hebert et al. |
| 2008/0076722 A1 | 3/2008 | Roberts et al. |
| 2008/0077175 A1 | 3/2008 | Palmer |
| 2008/0091174 A1 | 4/2008 | Alam et al. |
| 2008/0095760 A1 | 4/2008 | Toombs |
| 2008/0109031 A1 | 5/2008 | Sepetka et al. |
| 2008/0114393 A1 | 5/2008 | Carrison et al. |
| 2008/0119888 A1 | 5/2008 | Huffmaster |
| 2008/0167678 A1 | 7/2008 | Morsi |
| 2008/0183198 A1 | 7/2008 | Sepetka et al. |
| 2008/0183206 A1 | 7/2008 | Batiste |
| 2008/0188885 A1 | 8/2008 | Sepetka et al. |
| 2008/0206134 A1 | 8/2008 | Lo et al. |
| 2008/0249409 A1 | 10/2008 | Fraser et al. |
| 2008/0262487 A1 | 10/2008 | Wensel et al. |
| 2008/0262528 A1 | 10/2008 | Martin |
| 2008/0262532 A1 | 10/2008 | Martin |
| 2008/0264216 A1 | 10/2008 | Duffy |
| 2008/0269871 A1 | 10/2008 | Eli |
| 2008/0275464 A1 | 11/2008 | Abrams et al. |
| 2009/0069828 A1 | 3/2009 | Martin et al. |
| 2009/0105722 A1 | 4/2009 | Fulkerson et al. |
| 2009/0105737 A1 | 4/2009 | Fulkerson et al. |
| 2009/0125053 A1 | 5/2009 | Ferrera et al. |
| 2009/0192518 A1 | 7/2009 | Golden et al. |
| 2009/0287291 A1 | 11/2009 | Becking et al. |

(56) References Cited

U.S. PATENT DOCUMENTS

| | | |
|---|---|---|
| 2009/0299393 A1 | 12/2009 | Martin et al. |
| 2010/0076452 A1 | 3/2010 | Sepetka et al. |
| 2010/0100106 A1 | 4/2010 | Ferrera |
| 2010/0174309 A1 | 7/2010 | Fulkerson et al. |
| 2010/0185210 A1 | 7/2010 | Hauser et al. |
| 2010/0217187 A1 | 8/2010 | Fulkerson et al. |
| 2010/0256600 A1 | 10/2010 | Ferrera |
| 2010/0318097 A1 | 12/2010 | Ferrera et al. |
| 2011/0160742 A1 | 6/2011 | Ferrera et al. |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0160763 A1 | 6/2011 | Ferrera et al. |
| 2011/0166588 A1 | 7/2011 | Sepetka et al. |
| 2011/0288572 A1 | 11/2011 | Martin |
| 2011/0319917 A1 | 12/2011 | Ferrera et al. |
| 2012/0143230 A1 | 6/2012 | Sepetka et al. |
| 2012/0197285 A1 | 8/2012 | Martin et al. |

FOREIGN PATENT DOCUMENTS

| | | |
|---|---|---|
| DE | 10 2004 040 868 A1 | 3/2006 |
| DE | 10 2005 059 670 A1 | 6/2007 |
| EP | 0200668 | 11/1986 |
| EP | 1312314 A1 | 5/2003 |
| JP | 2001-517527 | 10/2001 |
| JP | 2002-537943 | 11/2002 |
| JP | 2003-530944 | 10/2003 |
| JP | 2008-539958 | 11/2008 |
| WO | WO 2000/053120 | 5/1994 |
| WO | WO 1995/009586 | 4/1995 |
| WO | WO 1996/001591 | 1/1996 |
| WO | WO 1996/017634 | 6/1996 |
| WO | WO 1996/019941 | 7/1996 |
| WO | WO 1997/027808 | 8/1997 |
| WO | WO 1997/027893 | 8/1997 |
| WO | WO 1998/003120 | 1/1998 |
| WO | WO 1999/016364 | 4/1999 |
| WO | WO 1994/009845 | 9/2000 |
| WO | WO 2000/072909 | 12/2000 |
| WO | WO 2001/032254 | 5/2001 |
| WO | WO 2001/054622 | 8/2001 |
| WO | WO 2001/067967 | 9/2001 |
| WO | WO 2001/080748 | 11/2001 |
| WO | WO 2002/002162 | 1/2002 |
| WO | WO 2002/028291 | 4/2002 |
| WO | WO 2003/000334 | 1/2003 |
| WO | WO 2003/061730 | 7/2003 |
| WO | WO 2003/089039 | 10/2003 |
| WO | WO 2006/031410 | 3/2006 |
| WO | WO 2006/084019 | 8/2006 |
| WO | WO 2007/092820 | 8/2007 |
| WO | WO 2007/136660 | 11/2007 |
| WO | WO 2007/143602 | 12/2007 |
| WO | WO 2008/034615 | 3/2008 |
| WO | WO 2008/036156 | 3/2008 |
| WO | WO 2008/063156 | 5/2008 |
| WO | WO 2008/072243 | 6/2008 |
| WO | WO 2008/086180 | 7/2008 |
| WO | WO 2008/097956 | 8/2008 |
| WO | WO 2008/097998 | 8/2008 |
| WO | WO 2008/113122 | 9/2008 |
| WO | WO 2008/127287 | 10/2008 |
| WO | WO 2008/131116 | 10/2008 |
| WO | WO 2009/034456 | 3/2009 |
| WO | WO 2009/086482 | 7/2009 |
| WO | WO 2011/091383 | 7/2011 |
| WO | WO 2012/009675 | 1/2012 |
| WO | WO 2013/106146 | 7/2013 |

* cited by examiner

METHODS FOR RESTORING BLOOD FLOW WITHIN BLOCKED VASCULATURE

CROSS-REFERENCE TO RELATED APPLICATIONS

This application is a continuation of U.S. application Ser. No. 11/684,546 filed Mar. 9, 2007, now abandoned, which is a continuation of U.S. application Ser. No. 11/671,450 filed Feb. 5, 2007, now abandoned, which is a non-provisional of U.S. Provisional Application No. 60/765,496 filed Feb. 3, 2006, each of which are incorporated by reference in their entirety.

FIELD OF THE INVENTION

The devices and methods described herein relate to clearing of blockages within body lumens, such as the vasculature, by addressing the frictional resistance on the obstruction prior to attempting to translate the obstruction within the body lumen. In one variation, the devices and methods described below may treat conditions of ischemic stroke by remove blockages within arteries leading to the brain. Accordingly, variations of such methods and devices must navigate tortuous anatomy and vasculature without causing unacceptable damage to the anatomy. Also, the devices and methods first secure and surround the obstruction (such as a clot) prior to significantly moving the clot within the anatomy.

BACKGROUND OF THE INVENTION

Ischemic stroke occurs when a blockage in an artery leading to the brain causes a lack of supply of oxygen and nutrients to the brain tissue. The brain relies on its arteries to supply oxygenated blood from the heart and lungs. The blood returning from the brain carries carbon dioxide and cellular waste. Blockages that interfere with this supply eventually cause the brain tissue to stop functioning. If the disruption in supply occurs for a sufficient amount of time, the continued lack of nutrients and oxygen causes irreversible cell death (infarction). Accordingly, immediate medical treatment of an ischemic stroke is critical for the recovery of a patient.

The infarction may not develop or may be greatly limited, given a rapid clearing of the blockage to reestablish the flow of blood. However, if left untreated, ischemic stroke may lead to the permanent loss of brain tissue, and can be marked by full or partial paralysis, loss of motor control, memory loss, or death.

Several different diseases may lead to an ischemic stroke. Typically, deposition of cholesterol (artheroselerosis), formation of blood clots, or other objects in the vessels may disrupt blood flow and lead to ischemic stroke. Furthermore, the substances that cause the blockages may break free from larger vessels outside the brain and become lodged within narrower arteries closer to the brain embolism).

Ischemic stroke may be divided into thrombotic strokes and embolic strokes. A thrombotic stroke occurs when the building and rupturing of atheromatous plaque within the brain blocks cerebral arteries. Clinically referred to as cerebral thrombosis or cerebral infarction, this condition represents approximately 10% of all strokes. An embolic stroke occurs when a clot or emboli forms somewhere other than in the brain, such as in the cervical carotid artery or in the heart, and travels in the bloodstream until the clot becomes lodged and can not travel any further. When such a condition occurs in the arteries supplying the brain, the condition results in almost immediate physical and neurological effects.

While these are the most common causes of ischemic stroke, there are many other possible causes. Examples include use of drugs, trauma to the blood vessels of the neck, or blood clotting disorders.

Apart from surgical techniques, medical practitioners could address such blockages with the use of Tissue Plasminogen Activator (t-PA). However, t-PA must be used within the first three hours of the onset of stroke symptoms and may take hours or even days to successfully restore flow. In addition, t-PA carries an increased risk of intracerebral hemorrhage. It is currently believed that the use of t-PA results in a 30% success rate as well as a 6% major complication rate. In view of these limitations, the majority of stroke patients in the U.S. do not receive t-PA treatment.

In addition, there are a number of surgical techniques used to remove blockages. For example, an embolectomy, involves incising a blood vessel and introducing a balloon tipped device (such as the Fogarty catheter) to the location of the occlusion. The balloon is then inflated at a point beyond the clot and used to translate the obstructing material back to the point of incision. The obstructing material is then removed by the surgeon. Concentric Medical, Inc. of Mountain View, Calif. supplies devices for an interventional approach to the removal of obstructions. Concentric supplies a Merci® Retriever system as a device based approach for the removal of clots. This system engages and ensnares a clot. Once captured, a balloon catheter inflates to temporarily halt forward blood flow while the clot is withdrawn. The clot, is then pulled into the catheter and out of the body.

Typically, the existing means to remove obstructions do not address the frictional forces that act on the obstruction during removal of the obstruction. For example, some conventional devices engage the clot from the distal (or downstream) side. As the device is pulled proximally (or upstream), the device attempts to either engulf or ensnare the clot. However, due to the consistency of the clot and because the clot is typically well lodged, within the vessel, the act of pulling, the clot in a proximal direction cause the clot to also compress in an axial direction. This axial compression (when viewed along the axis of the vessel) causes a contemporaneous radial expansion of the clot (when viewed relative to the vessel). As a result, the increase in diameter of the clot causes an increase in the frictional forces applied against the arterial wall. Thus, by not addressing the frictional forces acting on the obstruction, the process of removing the clot may actually increase the static force that would otherwise be required to remove or translate the clot within the vessel. Unfortunately, increasing the amount of force applied upon one side of the clot also increases the probability of complications during the procedure (e.g., fragmenting the clot, failing to remove the clot, failure to fully engulf/ensnare the clot, and/or device failure) and can cause potential damage to the surrounding vessel.

While there are other drugs and suppliers of devices for removal of blockages, there remains a need for methods and devices that improve the success rate and/or reduce the complication rate in restoring flow and thereby limit the damage from an ischemic stroke.

SUMMARY OF THE INVENTION

It should be noted that the present methods and devices may be used to treat blockages leading to ischemic stroke as well as to treat blockages (caused by "obstructions") within other parts of the body (i.e., unless specifically noted, the devices and methods are not simply limited to the cerebral vasculature). The term "obstructions" may include blood clot(s), plaque, cholesterol, thrombus, a naturally occurring, foreign body (i.e., a part of the body that is lodged within the human), a non-naturally occurring foreign body (i.e., a portion of a medical device or other non-naturally occurring substance lodged within the lumen).

In one variation of the devices described herein, the device allows for surrounding the obstruction prior to attempting to translate or move the obstruction within the vessel. It should be noted that although minimal axial movement of the obstruction may take place, the device surrounds the obstruction before such movement causes significant distortion to the geometry of the obstruction resulting in an increase in the static force required to remove the obstruction from the vessel.

In another variation of the device, the device may include a low friction mode (such as a set of parallel wires, or wires extending axially along the lumen or vessel) that converts to an increased friction mode (such as a compressed set of wires acting on the obstruction or a twisted set of wires acting on the obstruction). The increase in friction is an increase in the friction between the obstruction and the device (as opposed to the vessel wall. In some cases, the low friction mode is a low surface area mode and the high friction mode is a high surface area mode. When configured m the low friction mode, the device is better suited to engage the obstruction without the undesirable effect of prematurely mobilizing the obstruction or compacting the obstruction (e.g., when wires are slid across the obstruction in a transverse motion). Upon engaging the obstruction, the device will conform to a high fiction mode with respect to the obstruction (in some cases the device will have an increased surface area mode). This high fiction mode permits the device to better grip the obstruction for ultimate removal of the obstruction.

The operation of the devices and method described herein secure the obstruction, overcome the elastic forces of the obstruction, then remove the obstruction from the anatomy without losing or fractionating the obstruction. In one variation of the invention, this is accomplished by the obstruction removal device interacting with the obstruction in the following manner: (1) the traversing filaments traverse the obstruction by passing either through the obstruction or between the obstruction and the vascular wall; (2) the traversing portion is pulled proximally to engage the surrounding portion of the device around the obstruction, the surrounding portion engaging the obstruction without causing significant mobilization of the obstruction; (3) the obstruction removal device is pulled further proximally and the surrounding portion now mobilizes the obstruction.

As shown below, variations of the devices have a configuration that provides a path for a portion of the device to surround the obstruction. The paths are made using traversing filaments that allow for low frictional translation of a surrounding portion of the device over the obstruction without causing axial translation of the obstruction. This mechanism is described in more detail below.

Once in the proper position, a portion of the device (e.g., a surrounding portion) increases the frictional contact with the obstruction to disperse the pulling force more evenly across the obstruction. The increased points of contact allow for removal of the obstruction through tortuous anatomy while ensuring that the obstruction will not escape the encapsulation.

The surrounding portion may be fabricated in a variety of ways. For example, the surrounding portion may comprise one or more filaments. The surrounding portion may comprise a filter/bag, a coil, helical filament, a mesh structure, corrugated sheet, braided filaments, single wound or crossing filaments, tubes, membranes, films, solid wires, filled tubes, castings. Furthermore, the surrounding portion may have one or more ports, openings, slits, and/or holes. The surrounding portion may be made by photochemical etching, mechanical drilling, weaving, braiding, laser cutting, or other means.

It should be noted that reference to surrounding or securing the obstruction includes partially and/or fully surrounding, engulfing, encapsulating, and/or securing the obstruction. In any case, the surrounding portion engages the obstruction prior to translation of the obstruction within the lumen. As noted herein, a portion of the device may convert into a surrounding section (e.g., when traversing wires re-orient to increase the friction acting on the obstruction). Accordingly, the traversing section converts into a surrounding section.

The various devices described herein rely on a reduced profile for delivery and an expanded profile for ultimate removal of the clot. The devices, or components of the devices, may expand when released from a constraint, which allows the device, or component, to assume a predetermined shape. Alternatively, or in combination, the devices may be actuated to assume the expanded profiles. For example, the devices may be shape memory alloys that assume a profile when reaching a predetermined temperature (e.g., body temperature, or another temperature via delivery of energy to the shape memory alloy to trigger a phase change). Actuation may also include use any expandable member (such as a coiled spring, balloon, wedge, etc.) that mechanically or fluidly forces expansion of the device. These modes are well known by those skilled in the art and are intended to be within the scope of the disclosure. When combined with the inventive concepts disclosed herein, such combinations fall within the inventive scope of this disclosure.

As noted above, the filaments of the invention may be used to translate the device or may be used to form the surrounding section. Accordingly, the filaments may be single wound or crossing filaments, tubes, membranes, films, solid wires, filled tubes, castings or any similar structure. Moreover, the cross section of such filaments may vary as required (e.g., circular, oval, rectangular, square, or any such shape.) The filaments may be constructed from metals, polymers, composites, hydrogels, membranes, shape memory metals, shape memory polymers, or shape memory alloys, superelastic metals, superelastic polymers, or superelastic alloys, or combinations thereof. The filaments may have uniform diameters or varying diameters. The characteristics of the filament may be selected to better suit their required function. For example, they can be stiff, floppy, or even have different zones of flexibility. Moreover, the filaments may be braided or woven members, or the construction may provide that the filaments cross at one or many points in an overlapping, interwoven, criss-crossing or similar manner.

It should be noted that in some variations of the invention, all or some of the filaments (used in the surrounding portion of the device) can be designed to increase their ability to adhere to the obstruction. For example, the filaments of the surrounding portion may be coupled to an energy source (e.g., RF, ultrasonic, or thermal energy) to "weld" to the obstruction. Application of energy to the filaments may allow the surrounding portion to deform into the obstruction and "embed" within the obstruction. Alternatively, the filaments may impart a positive charge to the obstruction to partially liquefy the obstruction sufficiently to allow for easier removal. Alternatively, a negative charge could be applied to further build thrombus and nest the device for better pulling force. The filaments may be made stickier by use of a hydrophilic substance(s), or by chemicals that would generate a chemical bond to the surface of the obstruction. Alternatively, the filaments may reduce the temperature of the obstruction to congeal or adhere to the obstruction.

BRIEF DESCRIPTION OF THE DRAWINGS

Each of the following figures diagrammatically illustrates aspects of the invention. Variation of the invention from the aspects shown in the figures is contemplated.

DETAILED DESCRIPTION

It is understood that the examples below discuss uses in the cerebral vasculature (namely the arteries). However, unless specifically noted, variations of the device and method are not limited to use in the cerebral vasculature. Instead, the invention may have applicability in various parts of the body. Moreover, the invention may be used in various procedures where the benefits of the method and/or device are desired.

Figure 1:
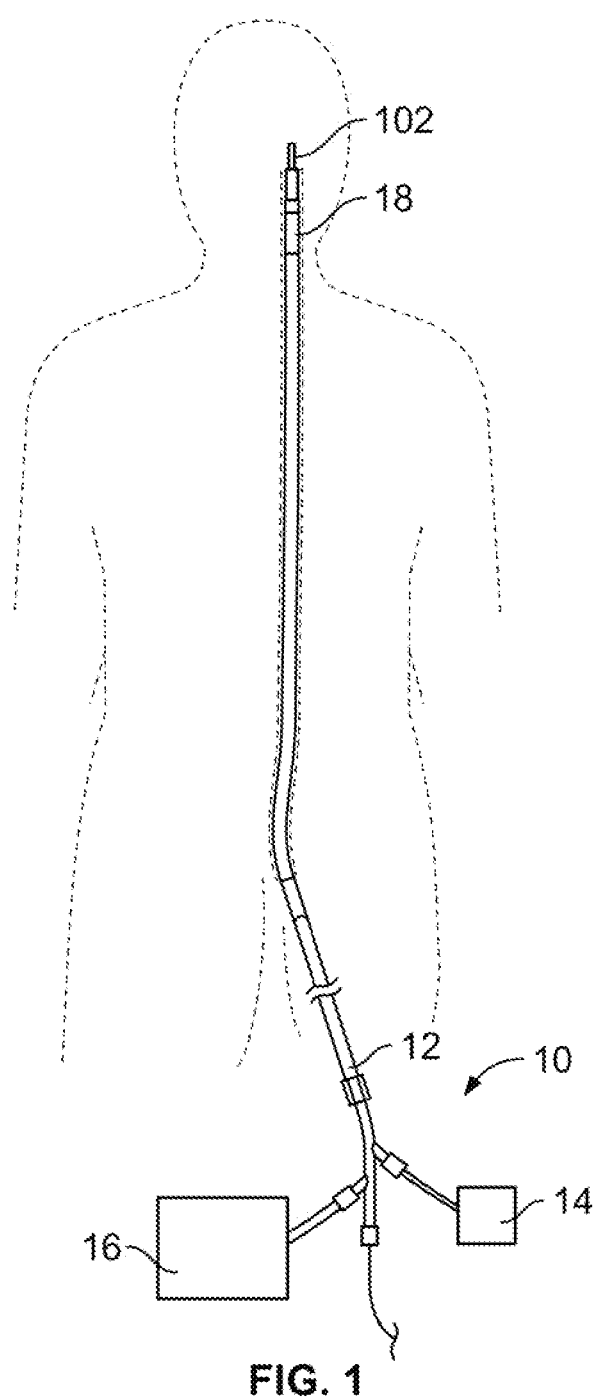
FIG. 1 illustrates a system for removing obstructions from body lumens.

FIG. 1 illustrates a system 10 for removing obstructions from body lumens as described herein. In the illustrated example, this variation of the system 10 is suited for removal of an obstruction in the cerebral vasculature. Typically, the system 10 includes a catheter 12 microcatheter, sheath, guide-catheter, or simple tube/sheath configuration for delivery of the obstruction removal device to the target anatomy. The catheter should be sufficient to deliver the device as discussed below. The catheter 12 may optionally include an inflatable balloon 18 for temporarily blocking blood flow or for expanding the vessel to release the obstruction It is noted that any number of catheters or microcatheters maybe used to locate the catheter/microcatheter 12 carrying the obstruction removal device (not illustrated) at the desired target site. Such techniques are well understood standard interventional catheterization techniques. Furthermore, the catheter 12 may be coupled to auxiliary or support components 14, 16 (e.g., energy controllers, power supplies, actuators for movement of the device(s), vacuum sources, inflation sources, sources for therapeutic substances, pressure monitoring, flow monitoring, various bio-chemical sensors, bio-chemical substance, etc.) Again, such components are within the scope of the system 10 described herein.

In addition, devices of the present invention may be packaged in kits including the components discussed above along with guiding catheters, various devices that assist in the stabilization or removal of the obstruction (e.g., proximal-assist devices that holds the proximal end of the obstruction in place preventing it from straying during removal or assisting in the removal of the obstruction), balloon-tipped guide catheters, dilators, etc.

FIGS. 2A to 2F show one example of the deployment of the basic structure of connectors and traversing filaments about an obstruction in a vessel. The figures are intended to demonstrate the initial placement of the connectors and filaments immediately prior to removal of the obstruction either using a filter or by torquing, rotating and/or twisting the near connector relative to the far connector. This action converts the device from a low friction device to a high friction device (where the low/high friction is the friction between the device and the obstruction). This action may also be referred to as a low surface area mode converting to a high surface area mode (in cases where the device extends beyond the obstruction and relative motion between ends of the device causes the device to shrink in axial length as it is twisted.) In addition, the number of connectors used, the shape of the connectors, as well as the number of filaments is intended to be for illustrative purposes only. It is contemplated that any variation of connector and/or filament may be deployed in a similar manner.

Figure 2A:
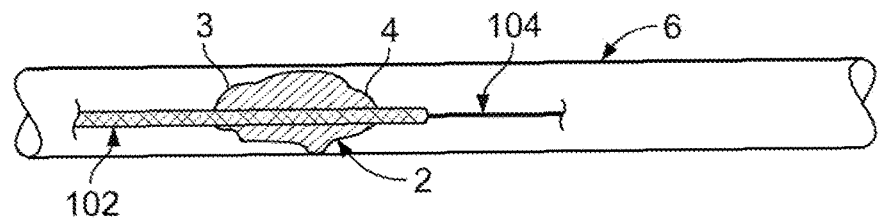
FIG. 2A illustrates an example of an obstruction lodged within a body lumen.

FIG. 2A illustrates an example of an obstruction 2 lodged within a body lumen or vessel 6. In the case where the vessel is a cerebral artery, the obstruction may result in an ischemic stroke. Using standard interventional catheterization techniques, a microcatheter 102 and guidewire 104 traverse the obstruction. The microcatheter 102 may be advanced through the obstruction 2. Alternatively, the microcatheter 102 may "push" aside the obstruction and is advanced around the obstruction. In any case, the microcatheter 102 travels from the near end 3 (or proximal side) of the obstruction 2 to the far end 4 (or distal side) of the obstruction 2. It is noted that the catheter 102 may be centered or off-center with respect to the obstruction 2. Furthermore, the device may or may not be used with a guidewire to navigate to the site and traverse the obstruction.

Figure 2B:
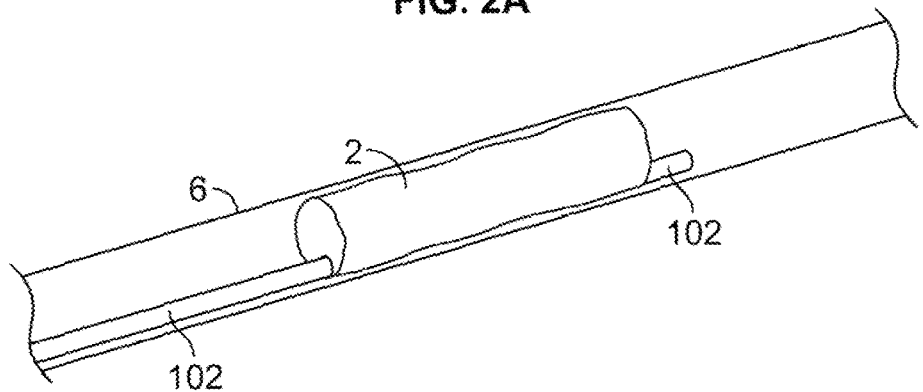
FIGS. 2B to 2F illustrate advancement of a catheter beyond an obstruction and placement of traversing wires around the obstruction.

FIG. 2B shows another variation where a microcatheter 102 traverses the obstruction 2 between the wall of the vessel 6 and the obstruction 2. As shown, the open end of the microcatheter 102 is distal to the obstruction 2 and is now positioned to deploy devices for removal of the obstruction 2. This variation shows the device after removal of any guidewire. However, some variations of the device may be placed without an accompanying guidewire. Moreover, the structures discussed herein may be directly incorporated into a guidewire assembly where deployment may require a sheath or other covering to release the components from constraint.

Figure 2C:
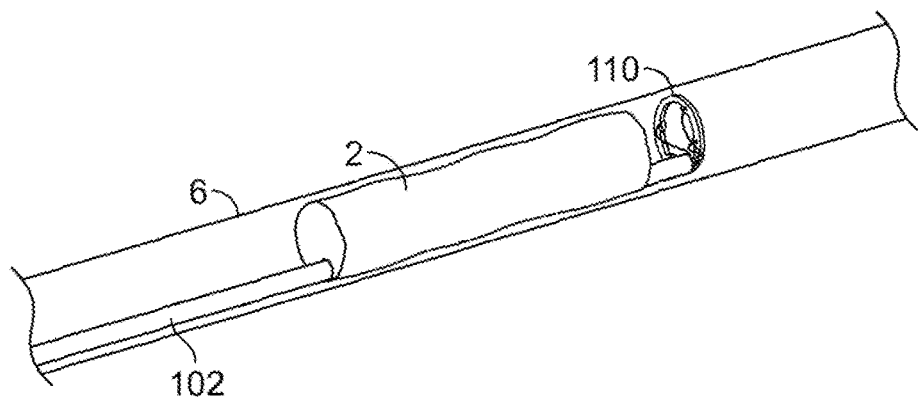

FIG. 2C illustrates deployment of a far connector 110 from within the microcatheter 102 distal to the obstruction 2. The far connector 110 can be self-expanding such that it assumes, or moves towards, the expanded profile as shown) upon deployment from the constraint of the microcatheter 102.

The connectors 108, 110 and/or traversing filaments 112 are designed to expand to the wall of the vessel when released from the catheter. This action allows the device 100 to surround the obstruction 2 prior to attempting to dislodge it. The components of the obstruction removal device 100 (e.g., the leading wires 106, the connectors 108 110, the traversing filaments 112, and/or the surrounding portion 114, may be fabricated from any biocompatible material that permits the function as described herein. In some variations, the material may comprise a shape memory or super-elastic alloy such as nitinol.

Figure 2D:
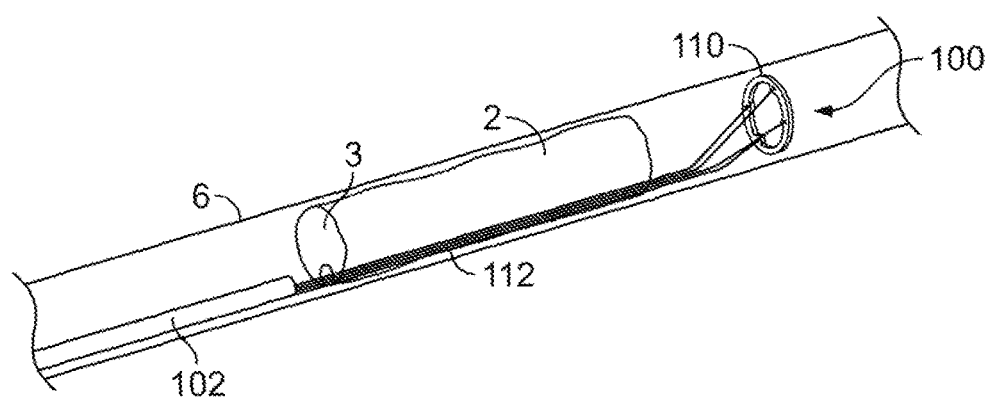

FIG. 2D shows withdrawal of the microcatheter 102 to the proximal side 3 of the obstruction 2. The spacing between the far connector 110 and the obstruction 2 may vary. In some cases, the far connector 110 will move closer towards the obstruction 2 during spacing of the traversing filaments 112 as discussed below. The far connector 110 remains in place either using the inherent friction of the connector against the vessels and/or obstruction 2. Alternatively, or in combination, a wire-type member (not shown) may provide an opposing, force against the connector 110 as the catheter 102 moves proximal to the obstruction 2.

As discussed herein, the obstruction removal devices include a plurality of filaments affixed between connectors. Since the far connector 110 is deployed at the distal side 4 of the obstruction 2, withdrawal of the microcatheter 102 results in the plurality of filaments 112 spanning across the obstruction 2 as shown.

Figure 2E:
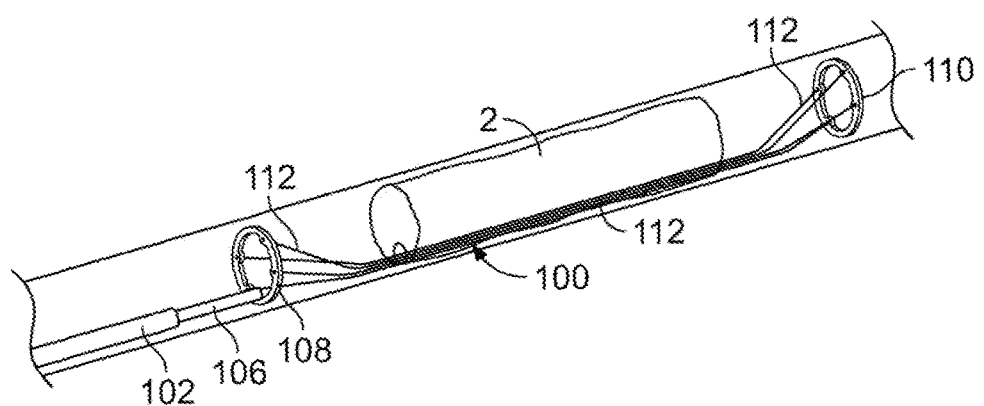

FIG. 2E illustrates deployment of a near connector 108. Although the illustrated variation depicts the near connector 108 as being deployed from within the microcatheter 102, alternative variations of the device include a near connector 108 that is located about the exterior of the microcatheter 102 or that is located about another delivery device (not shown) that is external to the microcatheter 102. In this case, the near connector 108 is similar in profile and design to the far connector 110. Accordingly, the near connector 108 self expands within the vessel 6 upon deployment from the microcatheter 102. In some variations of the device, the near and far connectors 108, 110 may have different shapes or profiles. In any case, the profile of the connectors should be sufficient to expand the traversing wires sufficiently within the vessel to prepare for ensnaring or encapsulation of the obstruction 2.

FIG. 2E also illustrates a connecting or leading wire/ member 106 that couples the microcatheter 102 to the near connector 108. The term leading wire, leading member, lead wire, etc. is intended to encompass a wire, tube, or any other structure that organizes and sometimes houses the smaller traversing filaments and/or near connectors described herein. Naturally, variations of the device include a leading wire 106 that is affixed to the far connector or the traversing wires. Moreover, the illustration depicts a single leading wire 106. However, as noted below, the device can include a number of traversing wire 106 affixed to the near and/or far connectors 108, 110.

Figure 2F:
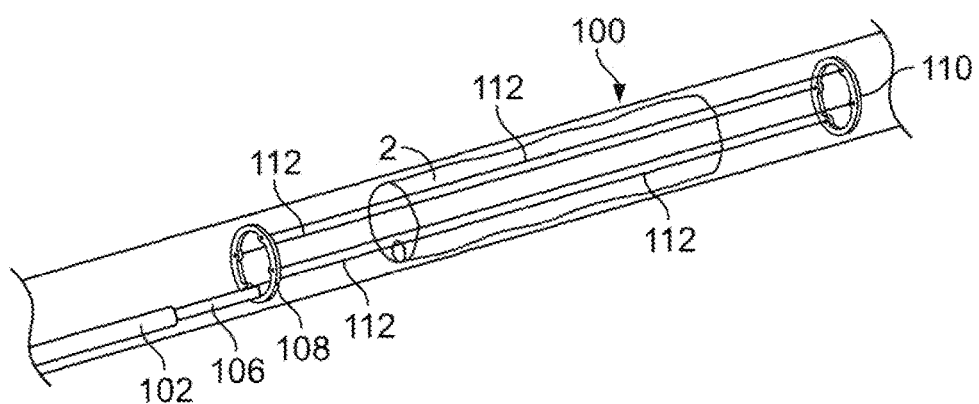

FIG. 2F illustrates spacing the traversing filaments/wires 112 from simply spanning the obstruction 2 (as depicted in FIG. 2E). This action causes the filaments 112 to span the obstruction 2 while reorienting towards an exterior of the obstruction 2. As noted herein, the traversing filaments 112 may remain partially or fully within the obstruction 2. However, given that the filaments are spaced about the connectors, the filaments shall separate radially over the obstruction allowing for the subsequent ensnaring and removal.

Spacing the filaments may occur via a number of modes such as tensioning, expanding, spreading separating and/or withdrawing the filaments. In certain variations of the device, the filaments are moveable relative to a near connector and/or a far connector. Such a feature allows application of tension to the filaments while keeping the connector in place. This causes the filament to enter a state of tension for spacing about the wall of the vessel. Alternatively, the filaments may be fixed relative to the connectors. Upon deployment, the filaments either self expand or are actuated to space about the vessel wall for eventual translation of the device over the obstruction. Regardless of the mode used, the filaments are intended to be positioned at or near a surface of the obstruction so that they can reduce the effects of any friction between the obstruction and the lumen or vessel wall.

Figure 3A:
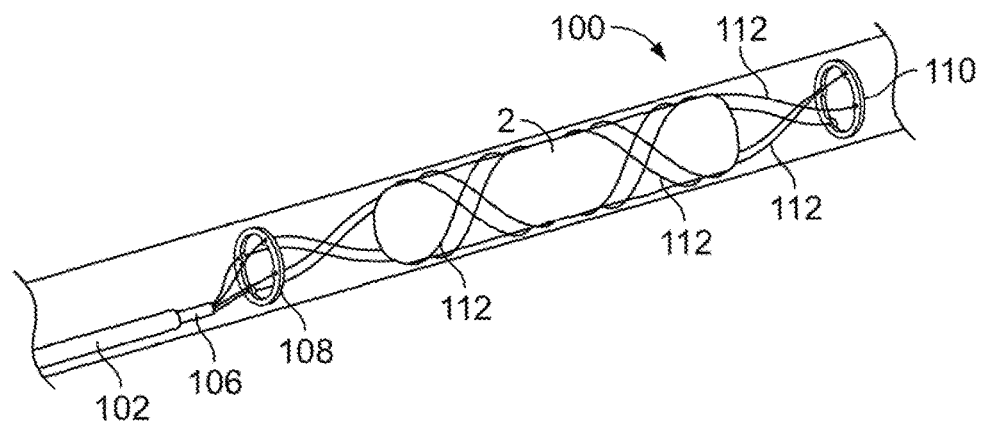
FIG. 3A illustrates an obstruction removal device once converted to a high friction mode.
Figure 3B:
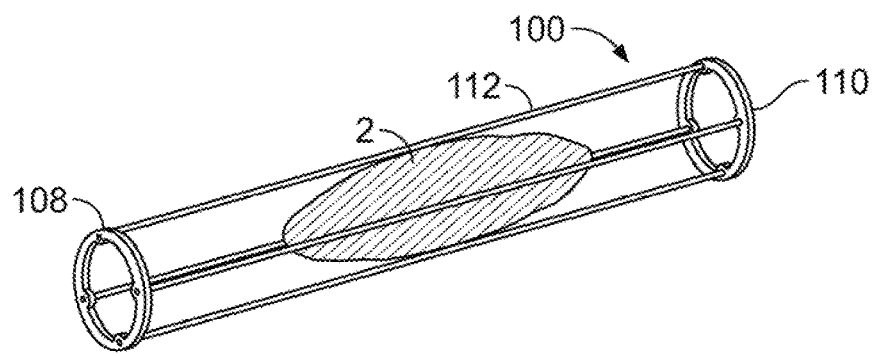
FIGS. 3B to 3E, show variations of a device having filaments that do not cross one another over the length of the obstruction when converted to a high friction mode.
Figure 3C:
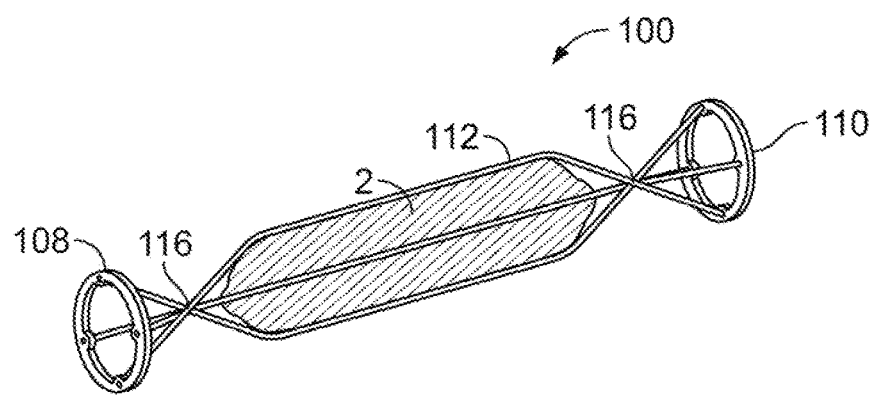
Figure 3D:
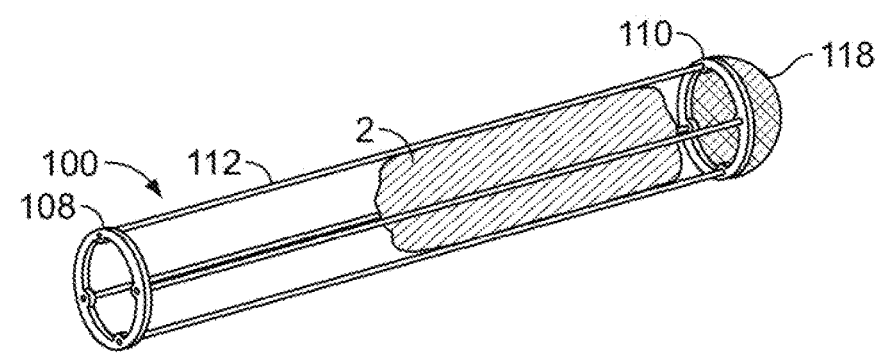
Figure 3E:
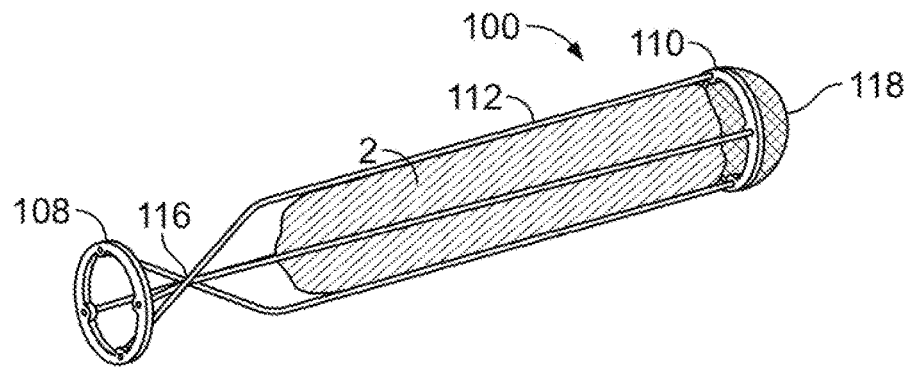
Figure 3F:
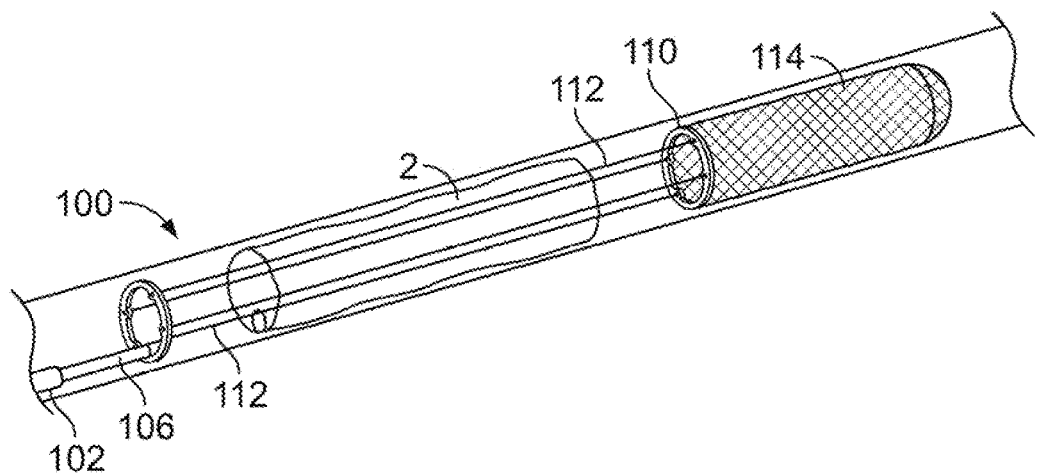
FIG. 3F to 3G illustrate positioning a surrounding portion and translating the surrounding portion over the obstruction.
Figure 3G:
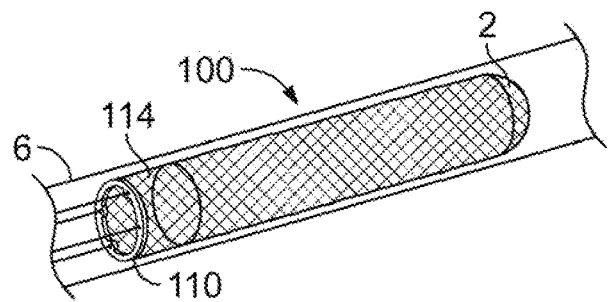

FIGS. 3A to 3I provide illustrations of device variations that ensnare the obstruction 2 after the device is in the configuration demonstrated by FIG. 2F above. FIGS. 3A, 3C, and 3E represent variations of the device 100 after transforming from a low friction mode to a higher friction mode for removal of the obstruction FIGS. 3F and 3G illustrate a variation where a surrounding portion or filter covers the obstruction for its ultimate removal from the body.

FIG. 3A illustrates rotation of the near connector 108 relative to the far connector 110 to ensnare the obstruction 2 within the traversing wires 112. As noted herein, either connector may rotate while another connector remains stationary. Alternatively, each connector may rotate with the rate of rotation for one connector being, slower than another. In yet another variation, each connector may be rotated in opposite directions.

Although the variation shows only four traversing, wires 112 any number of wires may be used so long as the rotation converts the traversing wires 112 into a relatively increased friction mode as compared to the low friction mode (when the traversing wires are in a parallel configuration). The low friction mode is represented by FIG. 2F. FIG. 3A illustrates the obstruction removal device 100 after rotation of the sets of traversing filaments and connectors. The result is that the obstruction 2 becomes ensnared (and/or encapsulated) and may be removed from the body. It should be noted that the same effect may be achieved by only rotating one connector or set of wires while keeping the other connector or set of wires stationary.

The rotation of the connector 108 can be performed in any number of ways as known to those skilled in the art.

However, as shown in FIG. 3A, the lead wire 106 may comprise additional secondary wires attached to the connector 108. So rotation of the connector 108 may occur via rotation of the lead wire and/or microcatheter. In any case, once the device assumes the increased friction mode condition, the obstruction 2 can be moved laterally within the vessel for removal.

FIGS. 3A to 3E illustrate various configurations where relative rotation of the connectors 108, 110 convert the device into a high friction mode. In FIG. 3A, the traversing filaments 112 twist and cross one another over the length of the obstruction 2. However, as shown in FIGS. 3B to 3E, variations of the device 100 can have filaments 112 that do not cross one another over the length of the obstruction 2. Although these variations are depicted to have single connectors on each end and four filaments, the design of the devices may vary as required by the particular application. In addition, the variations shown in FIGS. 3B to 3E are shown without any catheter or leading wire for convenience to better illustrate the conversion of the device from a low friction mode to a high friction mode. Naturally, rotation of the catheter and/or lead wire will cause relative rotation between connectors.

In FIG. 3B, the device 100 is in a similar position as that shown in FIG. 2E. However, FIG. 3B shows a variation of a device 100 that is selected to have a length greater than the targeted obstruction 2. Upon rotation, the traversing filaments 112 remain uncrossed over the length of the obstruction 2. In some cases, the filaments 112 may experience some twisting and will not remain parallel. However, the filaments 112 twist at twist points 116 that are proximal to and distal to the obstruction 2. The relative motion of the connectors 108, 110 as well as the twist point 116 causes the filaments 112 to exert a compressive force on the obstruction 2 without crossing one another over the length of the construction. Accordingly, while the surface area in contact between the filaments 112 and obstruction 2 remains relatively the same, the compressive action of the filaments 112 onto the obstruction converts the device 100 to a high friction mode on the obstruction.

FIG. 3D illustrates another variation of a device in a similar position as that shown in FIG. 2E. However, FIG. 3D shows a variation of a device 100 that extends proximally from the near end of the obstruction 2. The relative motion between connectors 108, 110 causes a twist point 116 that is proximal to the obstruction 2. As with the previous variation, the twist point 116 forces the filaments 112 against the obstruction 2 without crossing one another over the length of the obstruction 2. As a result, the device 100 is now in high friction mode. In some cases, the filaments 112 may experience some twisting and will not remain parallel.

The variation of FIGS. 3D and 3E also show the device 100 as including a cap or cover 118 about the distal connector 110. The cap or cover 118 may be a bag, mesh, a continuation of the filaments 112, and/or a surrounding, portion 114 as discussed herein. The cap or cover 118 reduces the likelihood that the obstruction is driven through the far connector 110 during conversion of the device 100 from a low friction mode to a high friction mode.

FIG. 3F illustrates another variation of a device where the far connector 110 includes a filter or surrounding portion 114. In variations of the device, the filter 114 is sufficiently permeable to allow blood flow therethrough. As noted above, the surrounding portion 114 may be any structure that covers, encapsulates, engulfs, and/or ensnares the obstruction either fully or partially. Accordingly, although the surrounding portion 114 is illustrated as a filter/bag, the surrounding portion 114 may comprise a coil, helical wire, a plurality of filaments, mesh structure, corrugated sheet, braided filaments, single wound or crossing filaments, tubes, filled tubes, castings, solid wires, membranes, films, capturing sections, (and may include ports, openings, slits, and/or holes made from photochemical etching, mechanical drilling) or any other structure that may translate or remove the obstruction 2 once the frictional component is addressed.

In this variation, the obstruction removal device 100 includes leading filaments 106 connected to a near connector 108. In this example, the lead filament 106 may be a single wire or filament. Alternatively, the lead filament may comprise a single wire with a plurality of wires connecting the single wire to the ring.

As with the above examples, the illustrated variation shows the connector 108 as comprising a loop. However, as described herein, the connectors may also comprise various alternate shapes (e.g., a circle, an arcuate shape, a partial circular shape, a loop, an oval, a square, a rectangle, a polygon, an overlapping loop, a pair of semi-circles, a flower shape, and a FIG. 8, other shapes, etc.) The near connector 108 is joined to a far connector 110 via a plurality of filaments 112. It is noted that the inventive device shall include at least one, but preferably two or more traversing filaments 112. It is further noted that the obstruction removal device 100 may be part of or integrated with the microcatheter 102.

FIG. 3G illustrates withdrawal of the microcatheter 102 and the proximal translation of device 100 to place the surrounding portion 114 over the obstruction 2. As the obstruction removal device 100 translates proximally, the traversing filaments 112 locate towards the exterior region of the obstruction 2. As discussed above, the connectors 108, 110 and traversing filaments 112 are designed to expand to (or near to) the perimeter of the wall of the vessel 2 and will usually locate to an exterior of the obstruction 2. However, variations of the device and method include situations where the filaments locate substantially, but not fully, towards the outer region of the obstruction. In any case, the location of the filaments 112 will sufficiently overcome the frictional forces discussed herein. In the illustrated variation, the traversing filaments 112 substantially span the length of the obstruction 2 by extending across the (proximal) 3 and (distal) 4 sides. These traversing filaments 112 provide paths for movement of the device 100 around the obstruction 2. These paths allow for the surrounding portion 114 to engulf the entire obstruction 2 so that it may be removed from the vasculature and body.

Figure 3H:
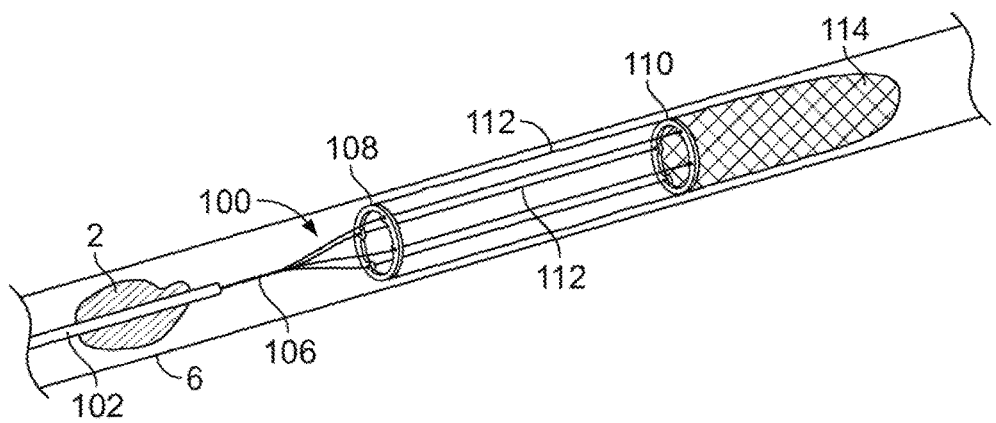
FIGS. 3H to 3I illustrate an obstruction removal device deployed distally to an obstruction and then translated proximally over the obstruction.

FIG. 3H depicts an obstruction removal device 100 similar to that shown in FIG. 3F. However, in this variation, the near and far connectors 108, 110 are both deployed distally to the obstruction 2 and then translated back over the obstruction 2. As shown, this deployment allows the traversing filaments 112 and the surrounding portion 114 to separate prior to contacting the occlusion 2. Next, the entire device 100 is pulled over the occlusion 2 as described above. The variation of the device shown in FIGS. 3F and 3H addresses the frictional forces that act between the obstruction and the vessel wall. Conventional devices that provide a bag attached to a wire (such as a vascular filter or distal protection device), are typically unable to remove the obstruction because they cannot overcome these frictional forces that lodge the clot against the vessel wall. Typically, such conventional devices are only designed to "catch" free floating clots. The traversing filaments described herein are configured to be positioned surrounding the obstruction. Their low friction with respect to the clot and the vessel allows for positioning of the filaments without disrupting or further compacting the clot against the vessel wall. Once the filaments surround or are spaced about the obstruction, they reduce the friction between the clot and vessel wall by reducing points of contact. Once these filaments surrounded the clot, they permit translation of the device to permit an encapsulating section 114 to surround the obstruction for removal.

Figure 3I:
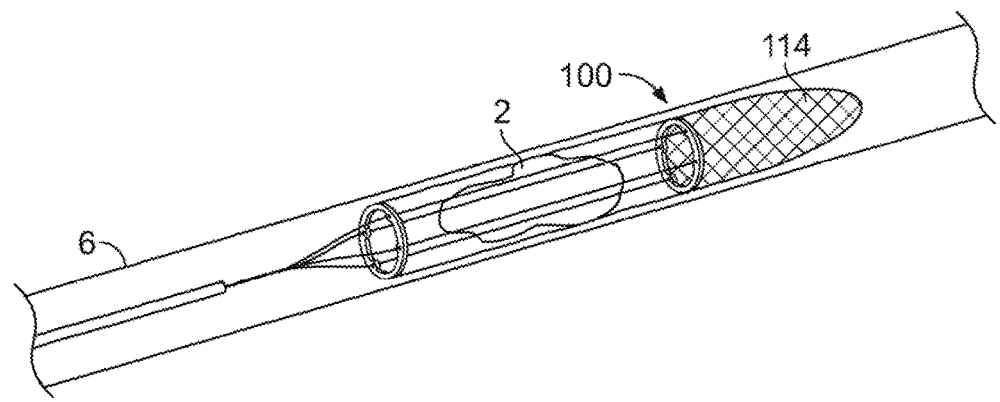

FIG. 3I illustrates the device 100 of FIG. 3H when translated over the obstruction 2. Eventually, the device 100 is pulled so that the surrounding portion or blood permeable filter 114 covers the obstruction 2 (as shown in FIGS. 3F and 3G.

Figure 4A:
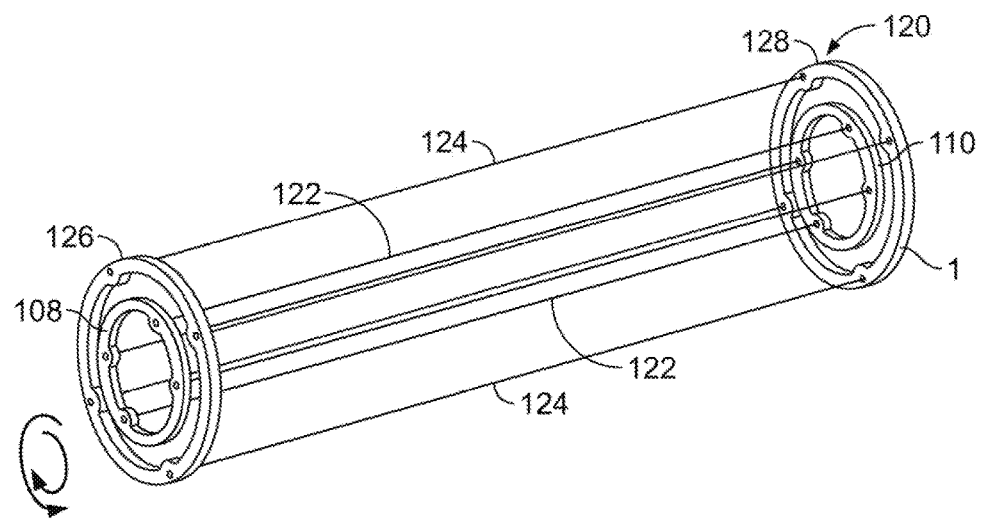
FIGS. 4A to 4E illustrate various additional configurations of devices able to assume a high friction mode covering over an obstruction.

FIG. 4A illustrates another variation of a portion of an obstruction removal device 120 that is able to convert from a low friction mode covering to a higher friction mode covering. As noted above, this variation allows the medical practitioner to engage an obstruction with sparse coverage or low friction mode to overcome frictional forces. Upon properly engaging the obstruction, the device configuration allows conversion to a high friction mode for removal of the device and obstruction.

As shown, this variation of the obstruction removal device 120 includes two sets of traversing filaments 122, 124 and accompanying connectors 108, 110, and 126, 128. The first set 122 comprises a first near connector 108 and first far connector 110 with the accompanying traversing filaments. The second set 124 comprises the second near connector 126 and second far connector 128 with the accompanying traversing filaments 124. The second set 124 is coaxially located over the first set 122. The materials of the components may be as described above. In any case, the components are designed to expand to the perimeter of the vessel wall upon release from the catheter.

Figure 4B:
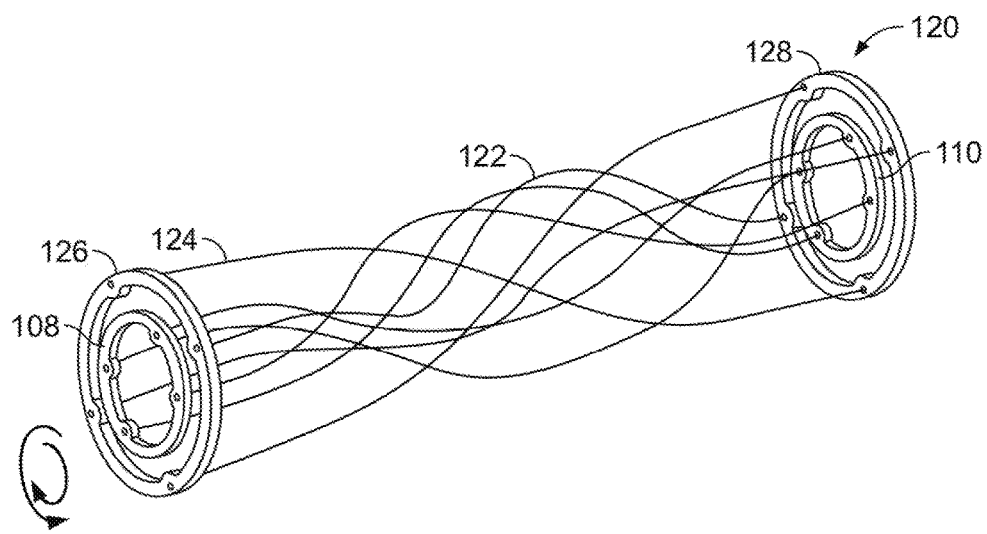

FIG. 4B shows the conversion of the obstruction removal device converting from a low friction mode (from FIG. 4A) to the high friction mode. For example, the first near connector 108 may be rotated relative to the second near connector 126 (where the second near connector may remain still or it may be rotated in an opposite direction relative to the first near connector as shown by the arrows). As a result, the traversing filaments 122, 124 deform in opposite directions to form a braid-type pattern increasing the friction mode over the obstruction.

Figure 4C:
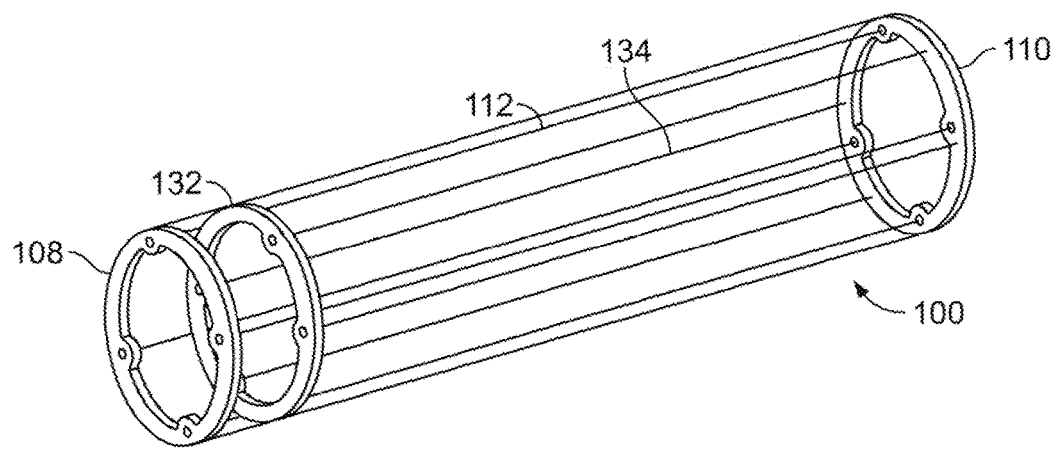
Figure 4D:
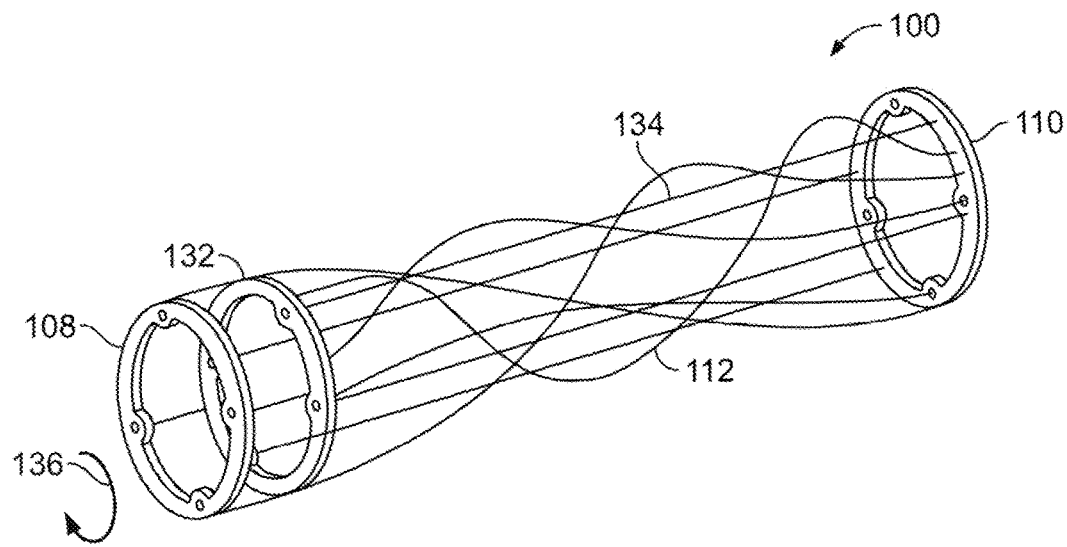

FIG. 4C illustrates another variation of an obstruction removal device 100 in a low friction mode state. In this variation, the device 100 includes a near connector 108, a far connector 110 with traversing filaments between the connectors 108, 110. The device 100 also includes an additional connector 132 with non-rotating filaments 134 extending to the far connector 110. FIG. 4D illustrates the device 100 of FIG. 4C when the near connector 108 is rotated as shown by arrow 136. However, the additional connector 132 and associated filaments 134 do not rotate. Upon rotation of the near connector 108 and twisting of the filaments 112, all of the filaments 112 and 134 compress the obstruction over the length of the filaments. Such a feature creates additional friction on the obstruction by the device.

Figure 4E:
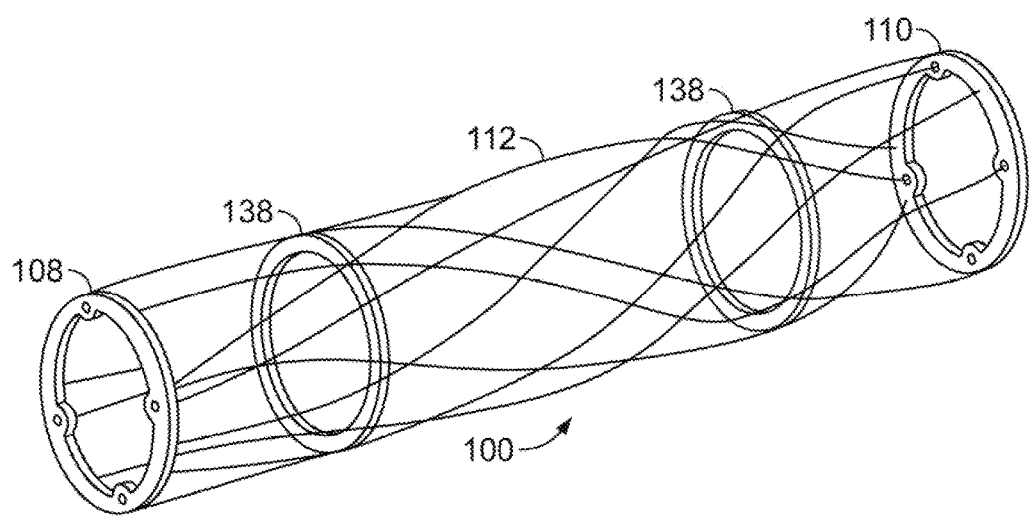

FIG. 4E shows another variation of an obstruction removal device 100 configured to move between low and high friction mode states. This variation includes additional support rings 138 located between connectors 108, 110 and within the filaments 112. The support rings keep the device 100 at a relatively constant diameter upon assuming the increased friction mode state. The support rings may be slightly undersized compared to the connectors, allowing the filaments to slightly compress the obstruction when converted to a high friction mode, but limiting the amount of compression by limiting the resulting diameter. The support rings 138 can be freely placed within the traversing filaments 112. Alternatively, the rings 138 can be attached to one or more than one filament 112 to prevent undesired migration during deployment of the device.

Figure 4F:
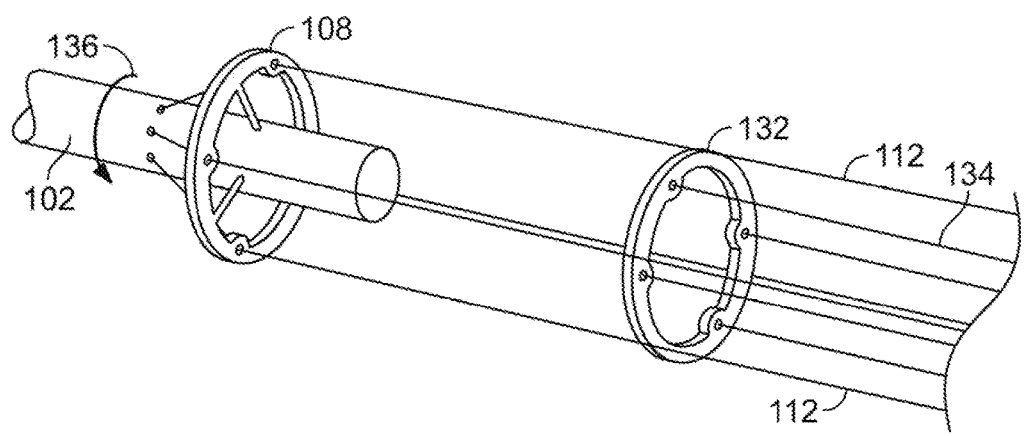
FIG. 4F illustrates a variation of a device using an end of a catheter for converting the device to a high friction mode.

FIG. 4F illustrates one example of a microcatheter 102 having a near connector 108 located externally to the catheter 102 with traversing filaments 112 extending out of the catheter and through the connector 108. In this variation, rotation or torquing of the catheter 102 twists the filaments 112 resulting in increased friction mode of the filaments 112 over an obstruction. FIG. 4F illustrates an additional connector 132 having stationary filaments 134. This variation of the device includes the external connector 108 directly coupled to a far connector not shown.)

Figure 5A:
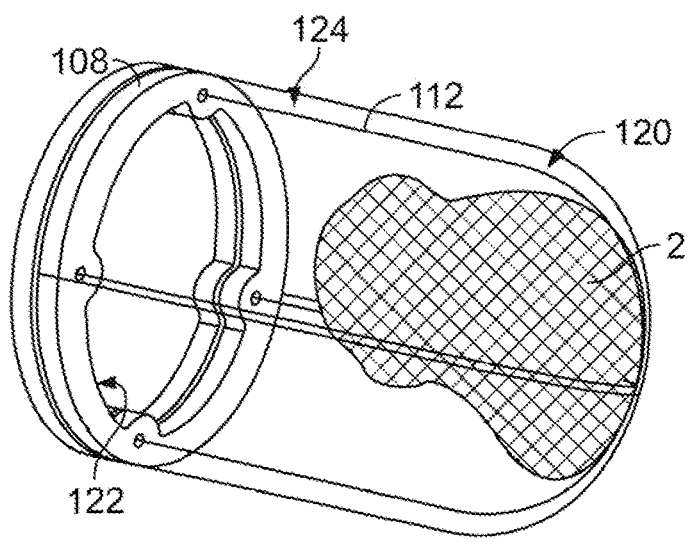
FIG. 5A to 5B illustrate another variation of a portion of an obstruction removal device configured to convert from a low friction mode to a high friction mode.
Figure 5B:
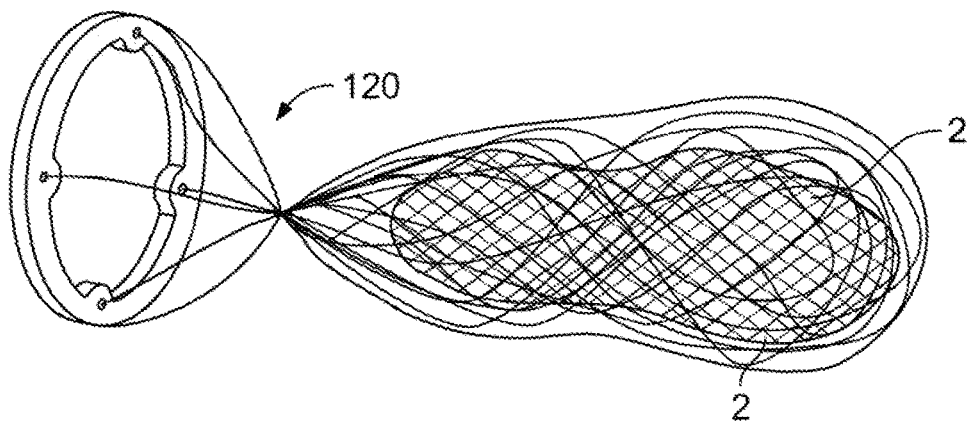

FIG. 5A illustrates a variation of the device 120 having only connectors 108 at one side of the device 120. In this variation, the device 120 may still include two sets 108, 122 of connectors and two sets of traversing filaments 112, 124. FIG. 5B illustrates the variation of FIG. 5A after conversion to a high friction mode over the obstruction 2. As discussed herein, the connectors may be other structures than loops. Moreover, variations of the invention include connectors that may be drawn down to a smaller size to facilitate removal from the body after securing the obstruction. This may be accomplished by torquing the device or pan thereof, by re-sheathing part or all of the device, or by any mechanical means designed into the features of the device itself. Any of these actions, or combination thereof, may also serve to compress or decrease the diameter of the obstruction itself to facilitate removal from the body.

In another variation, the devices described herein may be assembled or constructed in-situ. For example, components of the device may include connectors, portions of the connectors, traversing elements, and/or surrounding sections. Any combination of these components can be placed in sequential fashion. Doing so forms a completed structure from deployment of a number of individual components. The end result is the formation of a device as shown in the figures. Accordingly, such components of the device may be separately deployed in a manner that requires "assembly" of the components by a medical practitioner during the procedure.

Figure 6A:
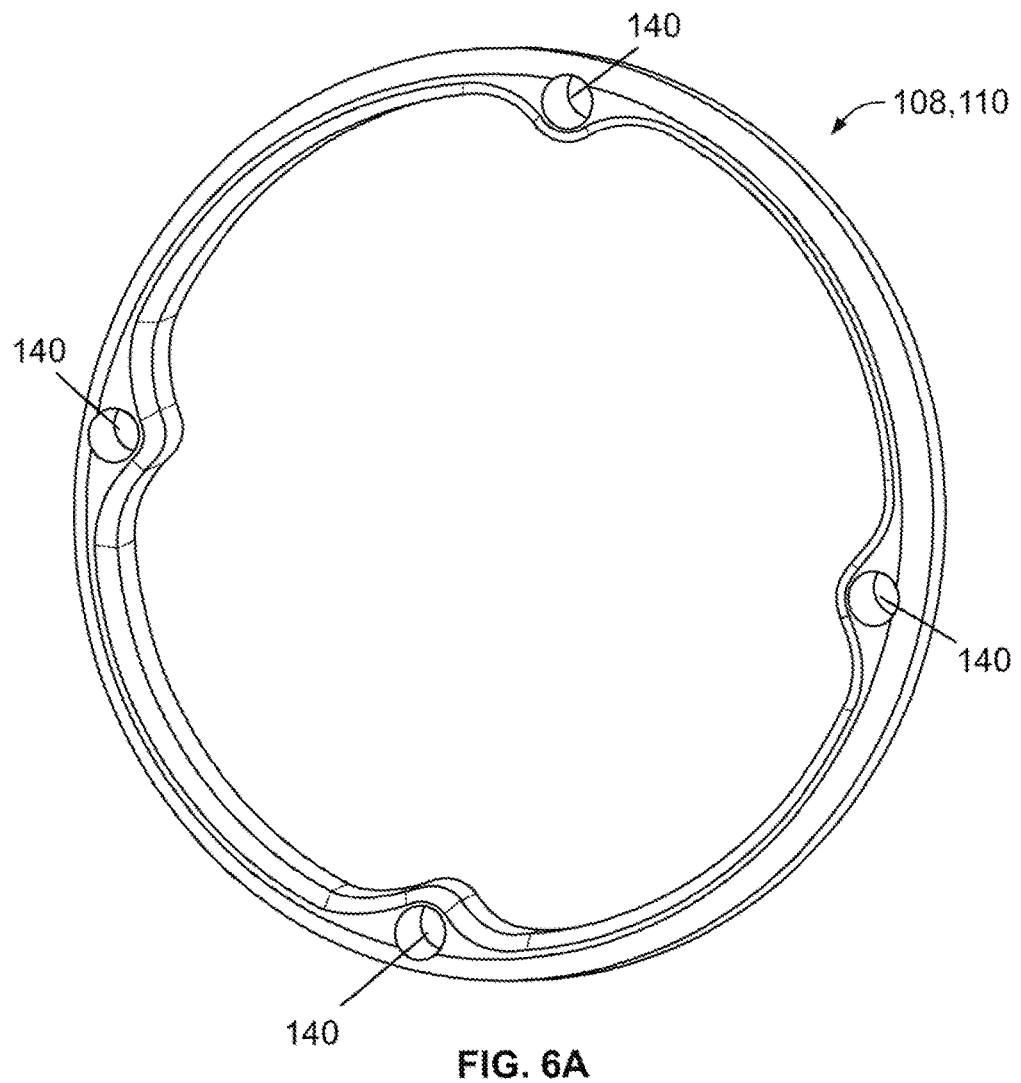
FIGS. 6A to 6G illustrate various configurations of connectors for use with obstruction removal devices.

FIGS. 6A-6G illustrate variations of the connectors 108, 110. FIG. 6A shows a loop-shaped connector 108, 110 having attachment points 140 for the filaments (not shown). As noted above, the connectors can be self-expanding or actuated to expand. The connectors may be fabricated from a polymer, a shape memory metal, polymer, or alloy, a super-elastic metal, polymer, or alloy, or any type of acceptable medical grade alloy, polymer, or composite structure. Also, the devices described herein can be fabricated from solid material, sheet or film, hollow or solid or filled rod or wire, braids, coils, etc. In the case of the polymer, additional strength may be added by constructing a composite layered device. For example, a hydrogel polymer with a hydrophilic fiber net inside that acts as exoskeleton to strengthen underlying polymer. As discussed herein, some variations of the device may include a distal connector having a cap or cover to prevent the obstruction from escaping as the device is removed. Furthermore, the sizing of the connectors within the vessel can assist in controlling relative rotation between connectors. For example, as a connector moves towards its expanded shape and engages a vessel or lumen wall, the rotational friction between the connector and lumen wall may prevent rotation. Accordingly, an adjacent connector may have a smaller expanded profile so that the connector experiences less friction when rotated.

FIG. 6A also illustrates the connector as having attachment points 140 for coupling the filaments to the connectors. These attachment points may allow for movement of the filaments relative to the connector to tension or separate the connectors (as described above.) The filaments may also be coupled such that they are fixed relative to the connectors. In such a case, pulling of the lead wire will cause the entire assembly (e.g., connectors, filaments, and/o surrounding portion) to translate through the vessel.

FIGS. 6B through 6G show various configurations of connectors for use in the present device. The connectors may be cut from sheets, fabricated from wire, molded, stamped, laser cut, photo or chemically etched, or fabricated in any other customary manner. Moreover, the connectors 108, 110 shown may be used in the near and/or far ends of the traversing wires. Different connector profiles may be incorporated into the device. In most cases, as shown, the connectors will form an arcuate shape so that they can expand against a vessel wall without causing trauma to the vessel. To illustrate the connector configurations, FIGS. 6B to 6E are shown without any accompanying traversing filaments.

Figure 6B:
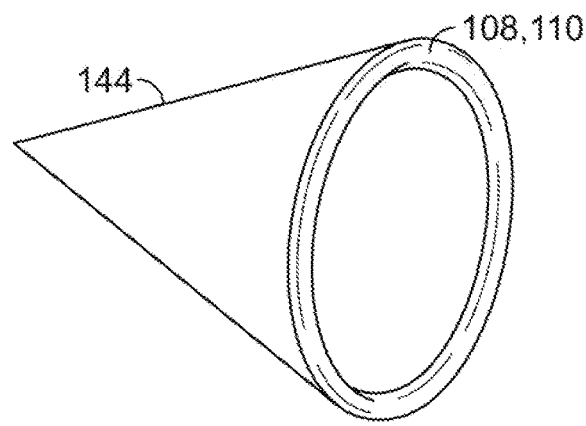
Figure 6C:
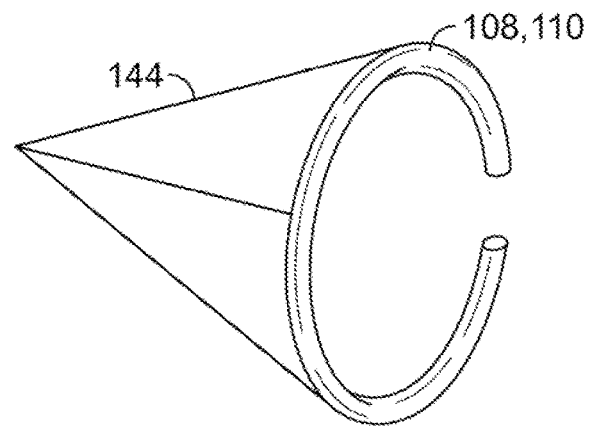
Figure 6D:
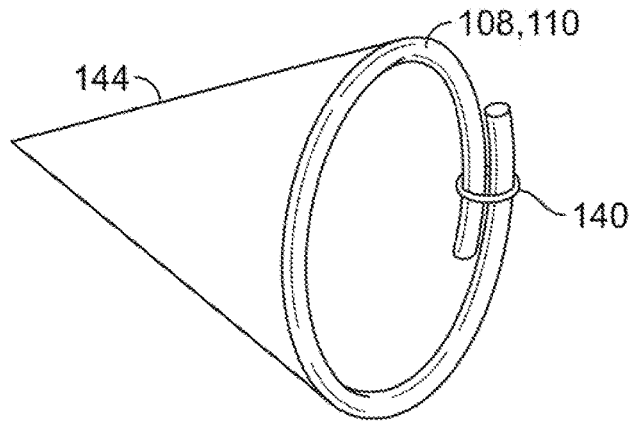

FIG. 6B shows a connector 108, 110 that is a loop shape as shown above. However, alternative configurations include a discontinuous profile, as illustrated in FIG. 6C and an overlapping profile, as illustrated in FIG. 6D. Such constructions allows the connector to adjust to varying diameters of body lumens. It is noted that a device may comprise loops of either construction. It should be also noted that although loops are shown, other variations may work equally well. Variations of the invention include connectors that may be drawn down to a smaller size to facilitate removal from the body once the obstruction is secured. This may be accomplished by torquing the device or part thereof, by re-sheathing part or all of the device or by any mechanical means designed into the features of the device itself. Any of these actions, or combination thereof, may also serve to compress or decrease the diameter of the obstruction itself to facilitate removal from the body. In addition, the overlapping connector, as shown in FIG. 6D, may include a sliding ring type fastener that allows the overlapping connector loop to expand in the same plane.

In another example, the device may be fabricated from a polymer composite that makes up the fasteners, filaments, bags, etc. where the polymeric composite is very floppy until it is exposed to either the body fluids and or some other delivered activator that causes the polymer to further polymerize or stiffen for strength. Various coatings could protect the polymer from further polymerizing before the device is properly placed. The coatings could provide a specific duration for placement (e.g., 5 minutes) after which the covering degrades or is activated with an agent (that doesn't affect the surrounding tissues) allowing the device to increase in stiffness so that it doesn't stretch as the thrombus is pulled out. For example, shape memory polymers would allow the device to increase in stiffness.

Figure 6E:
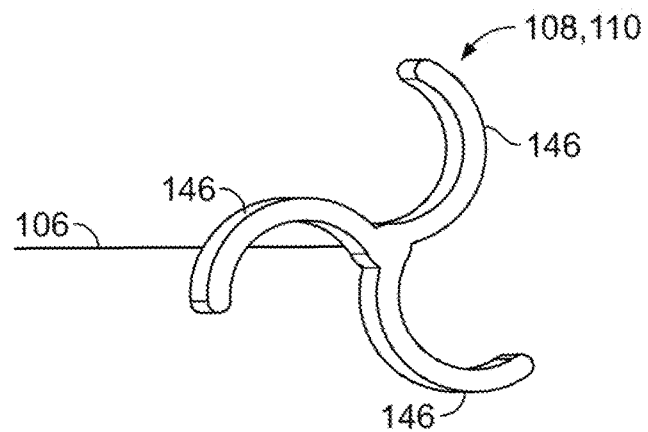

FIG. 6E shows a connector 108, 110 having multiple sections 146. As noted above, the connector sections 146 are arcuate shaped to minimize trauma to a vessel wall. However, other shapes are also intended to be within the scope of this disclosure.

FIGS. 6B through 6G also illustrate various configurations of leading wires 106. The connectors may have any number of leading wires. In some variations, it may be desirable to space the leading wires about the profile of the connector to aid in uniform movement of the device as it is pulled over the obstruction in the vessel.

Figure 6F:
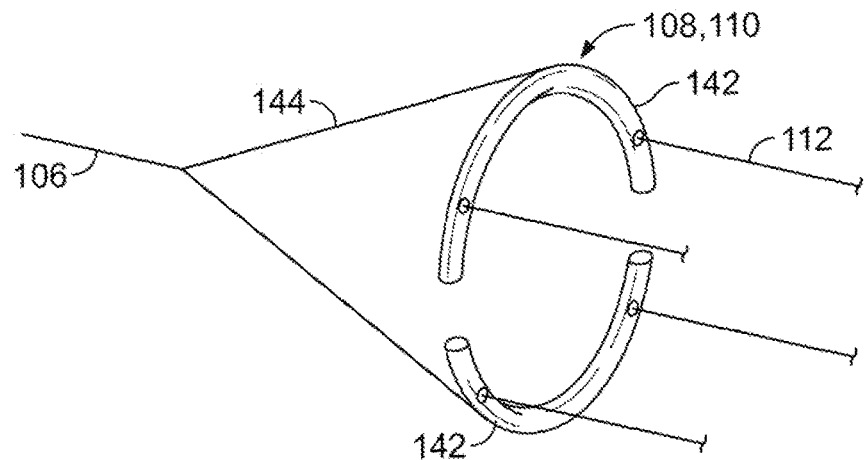
Figure 6G:
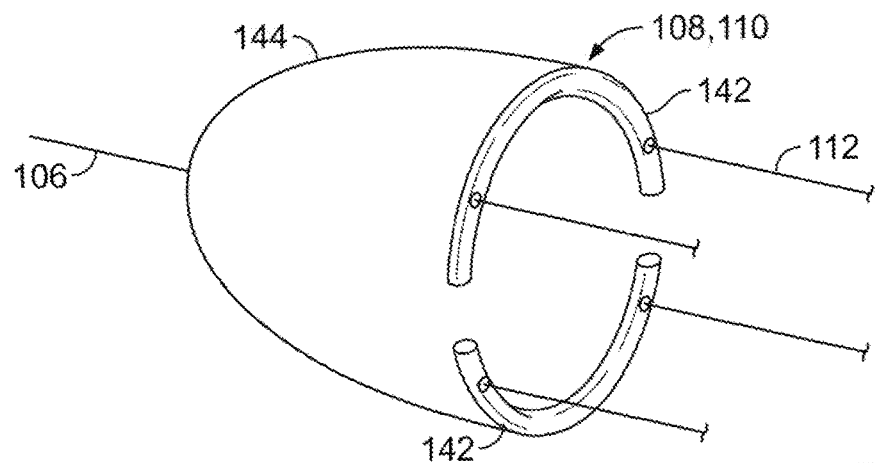

FIGS. 6F and 6G illustrate additional variations of leading wires 106 comprising shaped wire structures that form a "c" portion 142 of the connector. In one variation, when constrained the "c" shaped portions 142 move together to allow for deliver within the catheter. Upon release from the catheter, the portions 142 assume their resting shape and expand within the vessel. The connecting portions 142 can be selected to have a size that is slightly greater than that of the vessel. Sizing the device relative to the target vessel may assist in placing the connecting portions 142 and accompanying traversing wires 112 against the wall of the vessel.

FIG. 6G shows an additional variation where a portion 144 of a leading wire 106 also has a "c" or semi-circular shape. In this configuration, the "c" shaped portion 144 of the leading wire 106 can also be sized relative to the target vessel. Accordingly, the portion 144 of the leading wire 106 functions to drive the connecting portion 142 against the vessel wall, while the shape of the connecting portion 142 also drives the traversing wire 112 against the vessel wall.

Figure 6H:
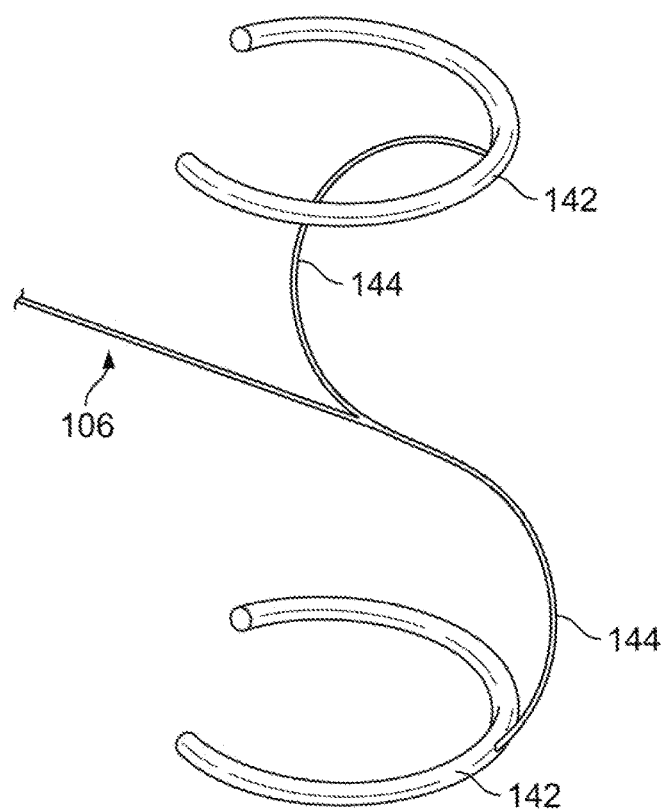
FIGS. 6H to 6I illustrate a variation of a leading wire and connector having an unconstrained shape that is selected to be larger or simply different than the intended vessel to provide increased, stability upon deployment.

FIG. 6H illustrates another variation of a leading wire 106 having an unconstrained shape that is selected to be larger than the intended vessel or simply different than a cross sectional profile of the intended vessel (i.e., not circular or tubular, but e.g., linear or other different shape). In this variation, the leading wire 106 has portions 144 that extend in opposite directions. This configuration is intended for illustrative purposes only. Variations include connecting portions pointing in an orthogonal direction from the main lead wire 106, oblique, parallel as shown), or a combination thereof. In any case, the unconstrained shape is intended to have a larger profile or size than the intended vessel. Moreover, the unconstrained shape may have an entirely different profile than the intended vessel. As shown in the figures, the profile of the device extends radially from the vessel. So when the device and leading wire are released, the leading wire attempts to return to the unconstrained shape. In those variations where the unconstrained shape is different from the circular profile of the vessel, the leading, wire assumes a shape that accommodates the vessel but is more rigid and stable since its unconstrained shape is entirely different from that of the vessel.

Figure 6I:
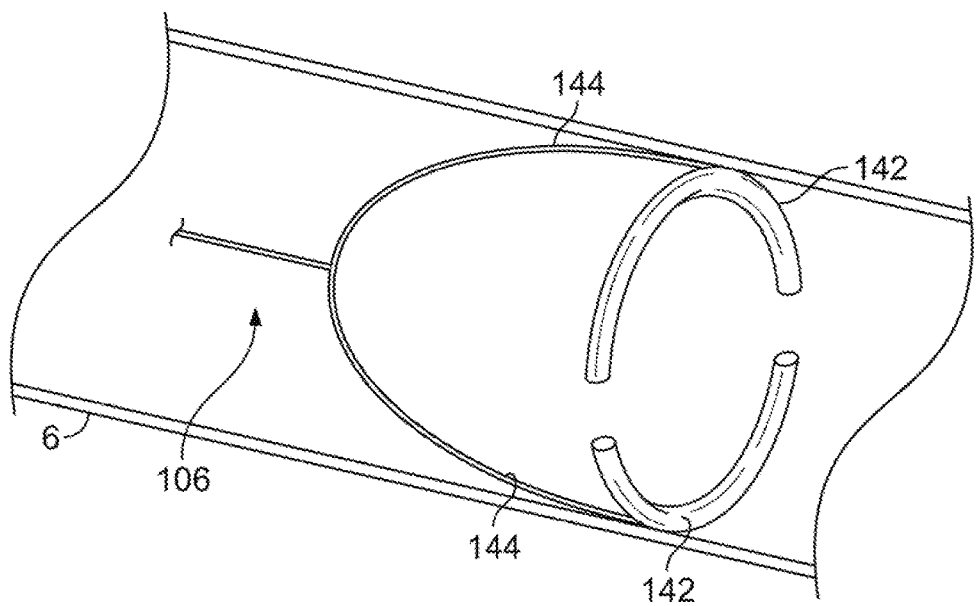

FIG. 6I shows the same device of FIG. 6H when released from a microcatheter, sheath, or tube when in the vessel. Once released, the leading wire 106 and accompanying portions 144 attempt to revert to the unconstrained shape (as shown in FIG. 6H). However, the vessel 6 restrains the leading wire 106 and portions 144 such that the portions 144 act on the walls of the vessel. This feature allows for improved stability when deploying the leading wires and attached connectors and filaments within the vessel.

Figure 7A:
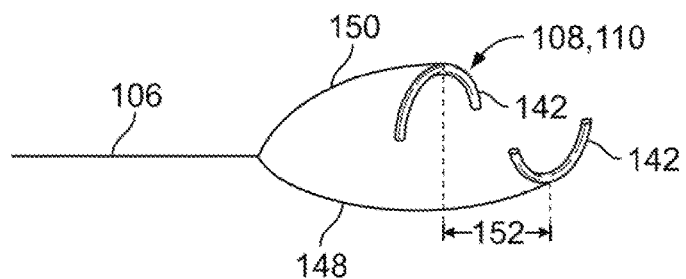
FIG. 7A to 7D illustrates variations in which the connector is offset.
Figure 7B:
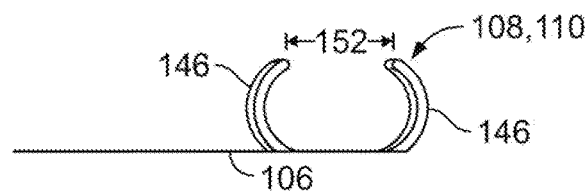
Figure 7C:
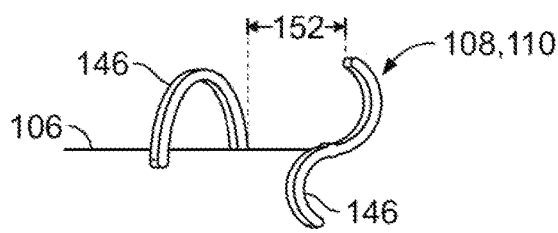
Figure 7D:
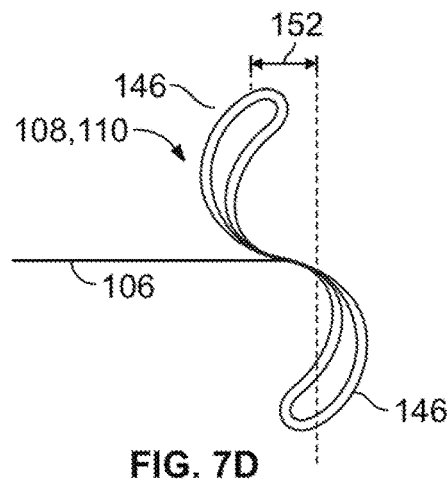

FIGS. 7A through 7C illustrate variations of connectors 108, 110 where the connector portions are axially spaced by an offset 152. One benefit of placing the connector portions 142, 146 in different planes is that the device may be delivered via a smaller microcatheter because the connector portions may be collapsed to a smaller diameter. FIG. 7A illustrates an offset 152 between connector portions 142 where each portion 142 is coupled to leading wires 148, 150 of varying lengths. FIG. 7B illustrates connector portions 146 spaced axially along a leading wire 106 to provide a gap 152. FIG. 7C illustrates a connector 108, 110 having multiple components 146 where one or more components is axially spaced to provide a gap 152. FIG. 7D shows a variation 108, 110 having a flower shape where each connector portion 146 is lion-planar such that the gap 152 occurs over the length of the connector portion 146.

Another aspect applicable to all variations of the devices is to configure the devices (whether the traversing filament or the surrounding portion) for better adherence to the obstruction. One such mode includes the use of coatings that bond to certain clots (or other materials causing the obstruction.) For example, the traversing filament and/or surrounding portion may be coated with a hydrogel or adhesive that bonds to a thrombus. Accordingly, as the surrounding portion covers the clot, or as the device twists about the clot, the combination of the additive and the mechanical structure of the device may improve the effectiveness of the device in removing the obstruction.

Figure 8A:
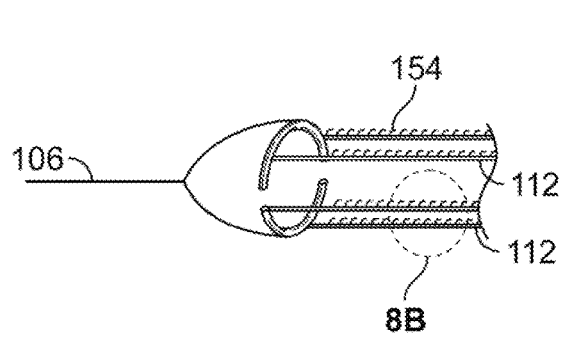
FIGS. 8A to 8B illustrate hooks, fibers, and/or barbs for increasing the ability of the device to remove obstructions.
Figure 8B:
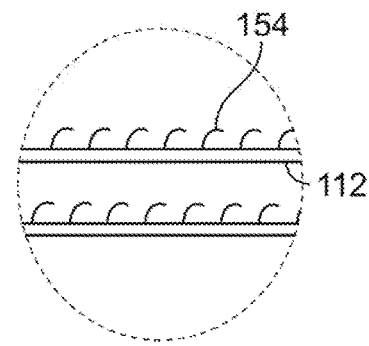

Such improvements may also be mechanical or structural. For example, as shown in FIG. 8A, the traversing members may have hooks, fibers, or barbs 154 that grip into the obstruction when the device converts to a high friction mode. The hooks, fibers, or barbs 154 may also be incorporated into the surrounding portion. However, it will be important that such features do not hinder the ability of the practitioner to remove the device from the body. For example, FIG. 8B illustrates a magnified view of the area 8B from FIG. 8A. As illustrated, the barbs may be configured such that rotation in a particular direction causes the barbs to adhere to the obstruction. Such a configuration could also allow lateral movement, without the barbs interfering with the vessel.

In addition to additives, the device can be coupled to an RF or other power source such as 14 or 16 in FIG. 1), to allow current, ultrasound or RF energy to transmit through the device and induce clotting or cause additional coagulation of a clot or other the obstruction.

The methods described herein may also include treating the obstruction prior to attempting to remove the obstruction. Such a treatment can include applying a chemical or pharmaceutical agent with the goal of making the occlusion shrink or to make it more rigid for easier removal. Such agents include, but are not limited to chemotherapy drugs, or solutions, a mild formalin or aldehyde solution.

Although not illustrated, the devices and methods described herein may also be useful in removing obstructions lodged within bifurcations in the anatomy. Generally, bifurcations greatly increase the frictional forces on the obstructions since the obstruction tends to be lodged in both branching sections of the bifurcation. In such cases, the use of the presently described devices and methods may also include an additional "puller" device that advances beyond the portion of the obstruction partially located in the bifurcated vessel.

As for other details of the present invention, materials and manufacturing techniques may be employed as within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

Figure 9A:
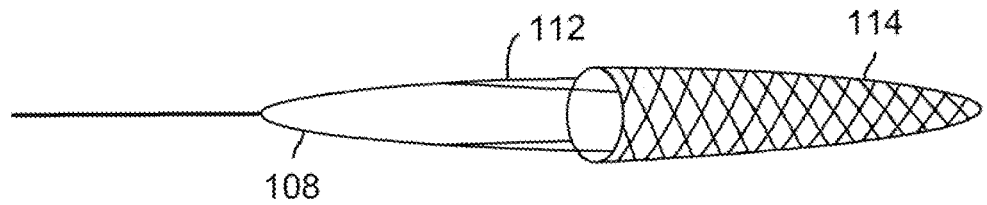
FIGS. 9A to 9C illustrate additional variations of obstruction removal devices.
Figure 9B:
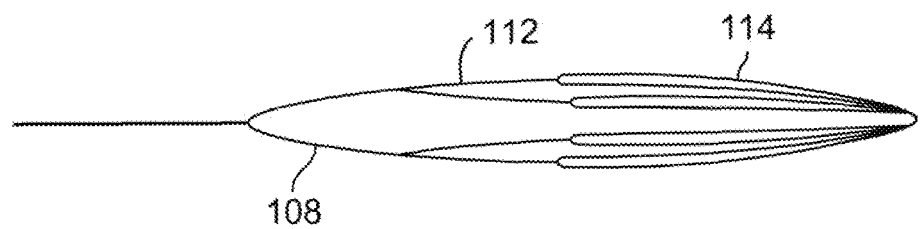
Figure 9C:
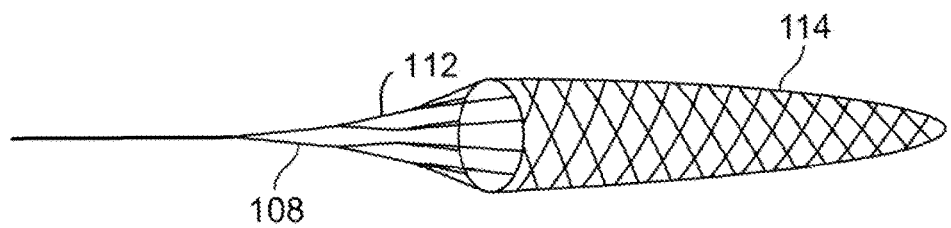
Figure 10A:
FIGS. 10A to 10H also illustrate additional variations of obstruction removal devices, focusing mainly on variations of the surrounding portion.
Figure 10B:
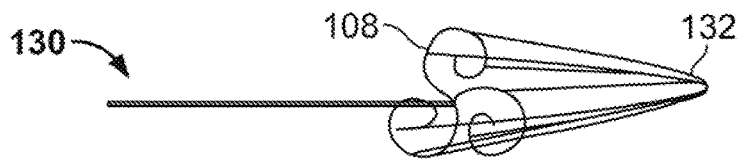
Figure 10C:
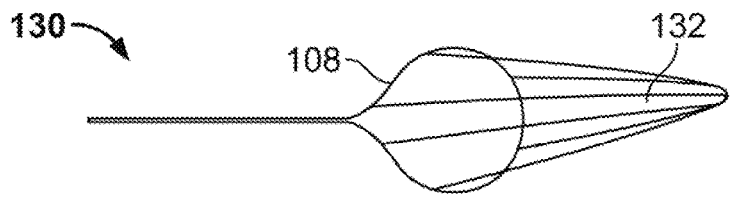
Figure 10D:
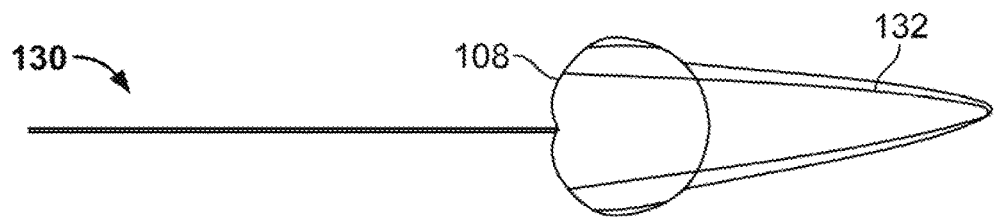
Figure 10E:
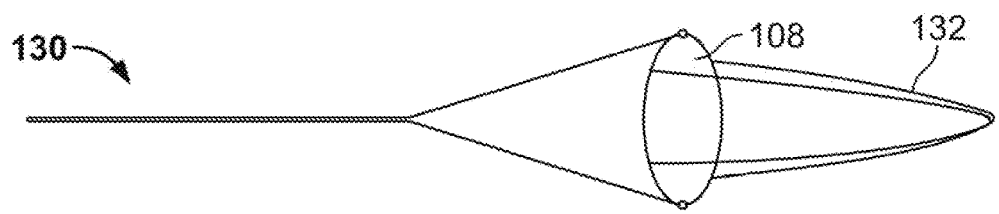
Figure 10F:
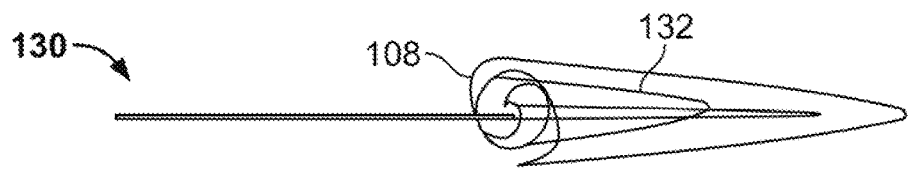
Figure 10G:
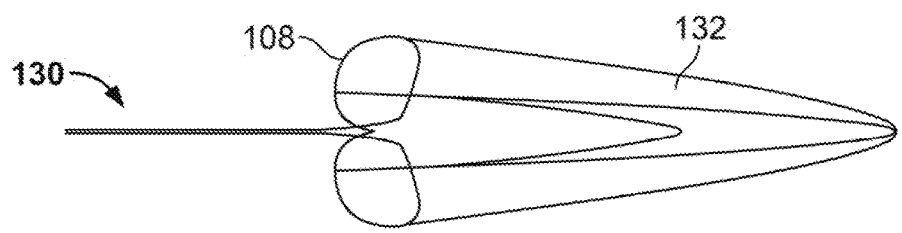
Figure 10H:
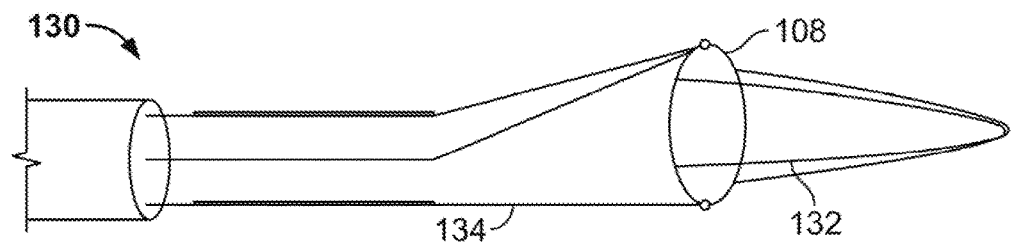

FIGS. 9A through 9C illustrate additional variations of obstruction removal devices. In these variations, the traversing filaments 112 may comprise a mesh of wires or single connector. FIGS. 9A to 9B illustrate a variation in which the connector 108 comprises a wire rather than a loop. However, the filaments and connectors should be configured to expand to the perimeter of the vessel wall as described previously.

FIGS. 10A-10H illustrate various additional embodiments of obstruction removal devices 130 according to the present invention. In these variations, the connector 108 may form a rigid wire or hard polymer to assist in placement of the device 130. The surrounding portion 132 may be fabricated from less rigid filaments that increase the point of contact with the obstruction. The surrounding portion may also have filaments that undergo a phase change from non-rigid for less rigid) to rigid.

It should be noted that any number of traversing filaments 112 or sets may be used in these variations.

Figure 11A:
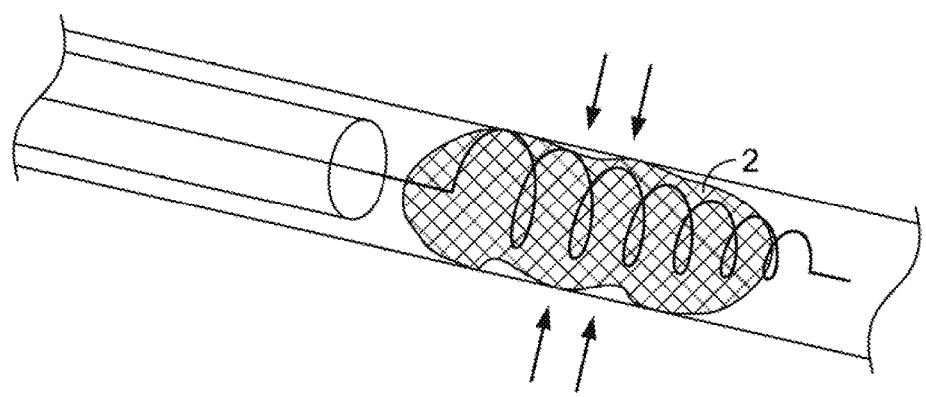
FIGS. 11A to 11C illustrate a variation where use of mechanical expansion distends the vessel wall and loosens the obstruction from the vessel.
Figure 11B:
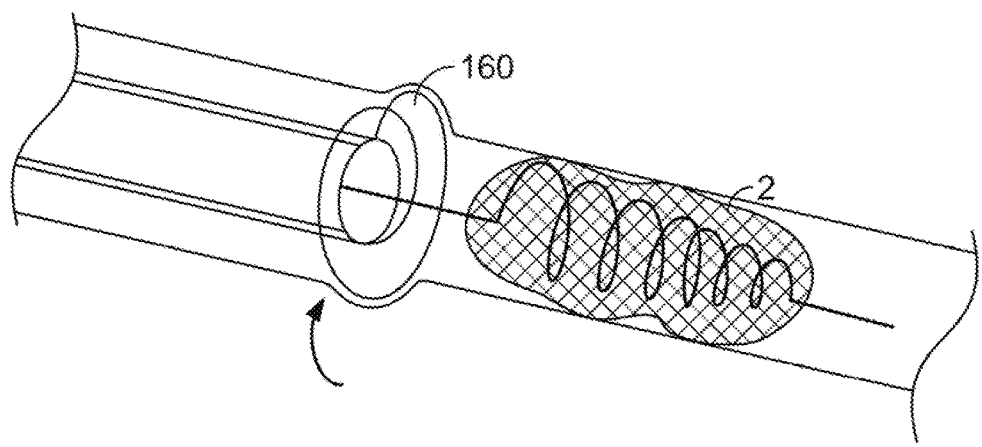
Figure 11C:
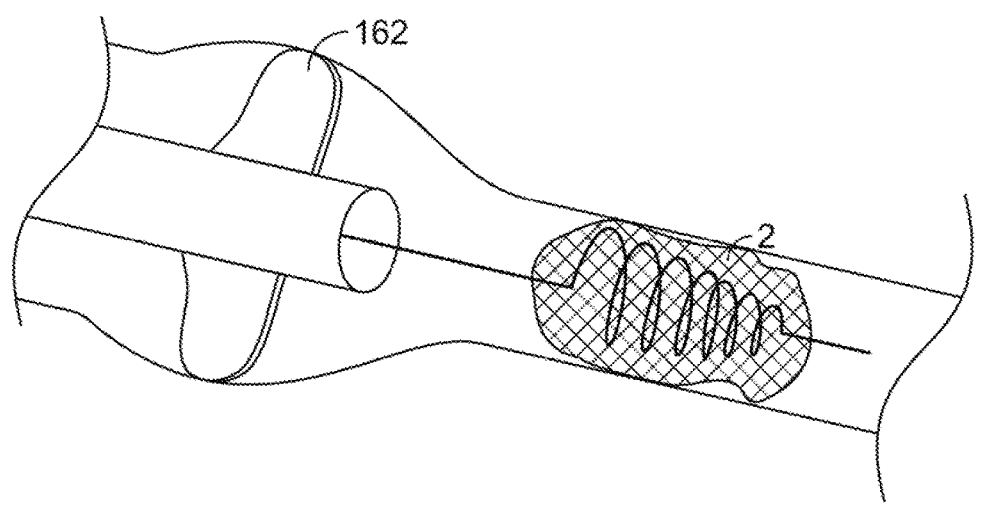

In additional aspect of the invention, as shown in FIG. 11A to 11C, the methods and or devices may include expansion of the vessel wall adjacent to the obstruction either with a balloon, coil, or similar mechanical expansion means, drugs, fluids, etc. Such an improvement may aid where the obstruction expands part, of the vessel wall thereby increasing the amount of force required for displacement. By distending the vessel wall as described above, the forces on the obstruction may be reduced allowing for ease of removal. FIG. 11A illustrates an obstruction 2 embedded within the vessel 6. FIGS. 11B to 11C illustrate variations where use of a coil (FIG. 11B) or a non-distensible balloon 162 (FIG. 11C) proximal to the obstruction 2 distends the vessel wall to loosen the obstruction 2 from the vessel. Accordingly, devices (whether described, herein or other conventional devices) may then remove the obstruction 2.

In those variations with a mechanical expansion means, the expansion means may be located on the delivery catheter of the obstruction removal device, on a wire member of the device, and/or on a separate catheter or wire used in combination with the first delivery catheter. However, variations of such configurations are within the scope of the invention.

In addition, devices and methods described herein may also use balloons proximal to the obstruction to stop or slow blood flow thereby preventing the blood from dislodging part or all of the obstruction.

Various changes may be made to the invention described and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "and," "said," and "the" include plural references unless the context clearly dictates otherwise.

We claim:

1. A method of improving blood flow in a blood vessel having an obstruction, the method comprising:
   advancing a microcatheter into the blood vessel, the microcatheter containing an obstruction removal device having an expandable structure located at the end of a leading member, the expandable structure including an intermediate portion extending between a proximal end and a distal end and including first and second regions, the expandable structure comprising a plurality of filaments and having a central longitudinal axis;
   positioning an opening of the microcatheter beyond a distal end of the obstruction;

deploying the distal end of the obstruction removal device beyond the distal end of the obstruction such that the distal end of the obstruction removal device self-expands towards the blood vessel wall;

withdrawing the microcatheter proximal to the obstruction while maintaining the expandable structure of the obstruction removal device in position such that the proximal and distal ends of the expandable structure span across the obstruction and where the proximal end self-expands within the vessel while spaced apart from the obstruction, thereby allowing the intermediate portion to embed into the obstruction;

holding the obstruction via the intermediate portion of the expandable structure between the first and second regions, wherein the filaments of the expandable structure converge radially inwardly toward the central longitudinal axis to meet within each of the first and second regions; and withdrawing the obstruction removal device and obstruction from the vessel to improve blood flow in the blood vessel.

2. The method of claim 1, further comprising positioning the obstruction removal device across the obstruction such that the obstruction removal device is initially offset from a longitudinal axis of the obstruction.

3. The method of claim 1, where deploying the distal end of the obstruction removal device beyond the distal end of the obstruction comprises withdrawing the microcatheter relative to the obstruction removal device such that the distal end of the obstruction removal device remains distal to the obstruction.

4. The method of claim 1, where allowing the intermediate portion to embed into the obstruction reduces a friction between the obstruction and a wall of the vessel.

5. The method of claim 1, where the expandable structure of the obstruction removal device is self-expanding.

6. The method of claim 1, where allowing the intermediate portion to embed into the obstruction comprises allowing the intermediate portion to embed into the obstruction without substantially dislocating or mobilizing the obstruction within the blood vessel.

7. The method of claim 1, where the obstruction removal device further comprises a surrounding portion attached to the distal end of the obstruction removal device and further comprising covering the obstruction with the surrounding portion.

8. The method of claim 7, where the surrounding portion comprises a structure selected from the group consisting of a basket, a filter, a bag, a coil, a helical wire structure, a mesh, a corrugated sheet, braided wires, a single wound wire, a plurality of crossing wires, a tube, a membranes, a filled tube, a solid wire, a casting, and a film.

9. The method of claim 1, where the obstruction removal device is fabricated from a process selected from the group consisting of a photochemical etching, mechanical drilling, weaving, braiding, and laser cutting.

10. The method of claim 1, further comprising advancing a catheter adjacent to the obstruction and where advancing the obstruction removal device comprises advancing the obstruction removal device and microcatheter through the catheter to the obstruction.

11. The method of claim 10, further comprising withdrawing at least a portion of the obstruction removal device within the catheter and removing the catheter from the vessel.

12. The method of claim 1, where the obstruction comprises a blood clot, plaque, cholesterol, thrombus, a naturally occurring foreign body, a non-naturally occurring foreign body or a combination thereof.

13. The method of claim 1, further comprising expanding the vessel adjacent to the obstruction to decrease a friction between the vessel and the obstruction.

14. The method of claim 1, where the intermediate portion forms a shaped section about the obstruction between the first and second regions.

15. The method of claim 1, where the proximal and distal ends of the expandable structure remain expanded towards the vessel wall when the first and second regions of the intermediate portion converge radially inwardly.

16. The method of claim 1 wherein the filaments are prevented from moving apart where they meet along the first and second regions.

17. A method of improving blood flow in a blood vessel having an obstruction, the method comprising:

advancing an obstruction removal device within the blood vessel where the obstruction removal device comprises an expandable structure with an intermediate portion extending between a proximal end and a distal end and including first and second regions, the expandable structure comprising a plurality of filaments and having a central longitudinal axis;

deploying the distal end and the proximal end of the expandable such that the expandable structure spans across the obstruction and the intermediate portion expands within the vessel to embed into the obstruction;

holding the obstruction via the intermediate portion of the expandable structure between the first and second regions, wherein the filaments of the expandable structure converge radially inwardly toward the central longitudinal axis to meet within each of the first and second regions; and withdrawing the obstruction removal device and obstruction from the vessel to improve blood flow in the blood vessel.

18. The method of claim 17, where the intermediate portion forms a shaped section about the obstruction between the first and second regions.

19. The method of claim 17, further comprising positioning the obstruction removal device across the obstruction such that the obstruction removal device is initially offset from a longitudinal axis of the obstruction.

20. The method of claim 17, where the expandable structure of the obstruction removal device is self-expanding.

21. The method of claim 17, where the obstruction removal device is fabricated from a process selected from the group consisting of a photochemical etching, mechanical drilling, weaving, braiding, and laser cutting.

22. The method of claim 17, further comprising withdrawing at least a portion of the obstruction removal device within a catheter and removing the catheter from the vessel.

* * * * *